United States Patent
Yan et al.

(10) Patent No.: US 12,329,987 B2
(45) Date of Patent: Jun. 17, 2025

(54) SYSTEMS AND METHODS FOR PATIENT POSITIONING DURING RADIOTHERAPY

(71) Applicants: The General Hospital Corporation, Boston, MA (US); Massachusetts Institute of Technology, Cambridge, MA (US)

(72) Inventors: Susu Yan, Boston, MA (US); Thomas Bortfeld, Cambridge, MA (US); Daniela Rus, Weston, MA (US); Thomas Buchner, Straubing (DE); Jay Flanz, North Andover, MA (US); Shuguang Li, Cambridge, MA (US)

(73) Assignees: The General Hospital Corporation, Boston, MA (US); Massachusetts Institute of Technology, Cambridge, MA (US)

( * ) Notice: Subject to any disclaimer, the term of this patent is extended or adjusted under 35 U.S.C. 154(b) by 187 days.

(21) Appl. No.: 17/781,470

(22) PCT Filed: Dec. 2, 2020

(86) PCT No.: PCT/US2020/062946
§ 371 (c)(1),
(2) Date: Jun. 1, 2022

(87) PCT Pub. No.: WO2021/113404
PCT Pub. Date: Jun. 10, 2021

(65) Prior Publication Data
US 2023/0051255 A1 Feb. 16, 2023

Related U.S. Application Data

(60) Provisional application No. 62/942,418, filed on Dec. 2, 2019.

(51) Int. Cl.
*A61N 5/10* (2006.01)
*A61B 5/11* (2006.01)
(Continued)

(52) U.S. Cl.
CPC .......... *A61N 5/1049* (2013.01); *A61B 5/1127* (2013.01); *A61B 6/0421* (2013.01);
(Continued)

(58) Field of Classification Search
CPC .......... A61N 5/1049; A61N 2005/1074; A61B 90/14; A61B 5/1127; A61B 6/0421; A61B 2090/101; A61B 2562/0252
See application file for complete search history.

(56) References Cited

U.S. PATENT DOCUMENTS

2005/0251914 A1 11/2005 Schaller et al.
2009/0131752 A1 5/2009 Park
(Continued)

FOREIGN PATENT DOCUMENTS

CN 101854848 A 10/2010
CN 101970048 A 2/2011
(Continued)

OTHER PUBLICATIONS

Almubarak, Y. et al., Design and Development of Soft Robot for Head and Neck Cancer Radiotherapy, In Electroactive Polymer Actuators and Devices (EAPAD) XX, Proc. of SPIE, 2018, vol. 10594, 9 pages.
(Continued)

*Primary Examiner* — David E Smith
(74) *Attorney, Agent, or Firm* — QUARLES & BRADY LLP

(57) ABSTRACT

A system and method for patient positioning during radiotherapy. The system can include a patient support structure configured to receive a patient during a radiotherapy process
(Continued)

using a radiotherapy source to deliver a therapy to the patient when positioned on the patient support structure, a patient positioning system configured to adjust a position of the patient support structure relative to the radiotherapy source, a flexible actuator configured to secure the patient to the patient support and adjust a position of the patient relative to the patient support, and an imaging system configured to acquire imaging data of the patient, the patient support, and the flexible actuator during the radiotherapy process.

22 Claims, 15 Drawing Sheets

(51) Int. Cl.
  *A61B 6/04* (2006.01)
  *A61B 90/10* (2016.01)
  *A61B 90/14* (2016.01)
(52) U.S. Cl.
  CPC ........ *A61B 90/14* (2016.02); *A61B 2090/101* (2016.02); *A61B 2562/0252* (2013.01); *A61N 2005/1074* (2013.01)

(56) References Cited

U.S. PATENT DOCUMENTS

| | | | |
|---|---|---|---|
| 2011/0313232 A1* | 12/2011 | Balakin | A61N 5/1081 315/503 |
| 2012/0305007 A1 | 12/2012 | Yan | |
| 2013/0025055 A1* | 1/2013 | Saracen | A61N 5/1049 901/29 |
| 2014/0238153 A1 | 8/2014 | Wood et al. | |
| 2015/0323302 A1 | 11/2015 | Chuang et al. | |

FOREIGN PATENT DOCUMENTS

| | | | |
|---|---|---|---|
| CN | 102781359 A | | 11/2012 |
| CN | 108356810 A | | 8/2018 |
| CN | 110471284 A | | 11/2019 |
| WO | WO-2017089457 A1 | * | 6/2017 |

OTHER PUBLICATIONS

Awad, L. et al., A Soft Robotic Exosuit Improves Walking in Patients After Stroke, Science Translational Medicine, 2017, 9(400):eaai9084, pp. 1-12.
Balakin, V. et al., Clinical Application of New Immobilization System in Seated Position for Proton Therapy, in the 2nd International Symposium on Physics, Engineering and Technologies for Biomedicine, KnE Energy & Physics, 2018, pp. 45-51.
Baumann, M. et al., Radiation Oncology in the Era of Precision Medicine, Nature Reviews Cancer, 2016, 16(4):234-249.
Belcher, A. et al., Development of a 6DOF Robotic Motion Phantom for Radiation Therapy, Medical Physics, 2014, 41(12):121704, pp. 1-7.
Best, C. et al., Control of a Pneumatically Actuated, Fully Inflatable, Fabric-Based, Humanoid Robot, In 2015 IEEE-RAS 15th International Conference on Humanoid Robots (Humanoids), pp. 1133-1140. IEEE, 2015.
Bortfeld, T. et al., Three Ways to Make Proton Therapy Affordable, Nature, 2017, 549(7673):451-453.
Buchner, T. et al., A Soft Robotic Device for Patient Immobilization in Sitting and Reclined Positions for a Compact Proton Therapy System, 2020 8th IEEE International Conference on Biomedical Robotics and Biomechantronics (BioRob), Dec. 1, 2020, pp. 981-988.
Buzorovic, I. et al., A Robotic Approach to 4D Real-Time Tumor Tracking for Radiotherapy, Physics in Medicine and Biology, 2011, 56(5):1299-1318.
Chen, C. et al., Proton Radiosurgery in Neurosurgery, Neurosurg Focus, 2007, 23(6):E5, pp. 1-5.
Cianchetti, M. et al., Soft Robotics Technologies to Address Shortcomings in Today's Minimally Invasive Surgery: The STIFF-FLOP Approach, Soft Robotics, 2014, 1(2):122-131.
Cianchetti, M. et al., Biomedical Applications of Soft Robotics, Nature Reviews Materials, 2018, 3(6):143-153.
CQ Medical, Vack-Lok(TM) Cushions, Nylon & Nylon with Indexing, 2019, https://civcort.com/ro/vaclok-and-cushioning/vaclok-cushions-nylon-nylon-w-indexing/miscellaneous-vaclok-cushions-V2.htm, 2 pages.
Deimel, R. et al., A Novel Type of Compliant and Underactuated Robotic Hand for Dexterous Grasping, International Journal of Robotics Research, 2016, 35(1-3):161-185.
Delcomyn, F. et al., Architectures for a Biomimetic Hexapod Robot, Robotics and Autonomous Systems, 2000, 30(1-2):5-15.
Felt, W. et al., Modeling Vacuum Bellows Soft Pneumatic Actuators with Optimal Mechanical Performance, In 2018 IEEE International Conference on Soft Robotics (RoboSoft), pp. 534-540.
Gough, V., Contribution to Discussion to Papers on Research in Automobile Stability, Control and Tyre Performance, Proc. of Automotive Division of the Institute of Mechanical Engineers, 1957, 171:392-395.
Hannan, M. et al., Kinematics and the Implementation of an Elephant's Trunk Manipulator and Other Continuum Style Robots, Journal of Robotic Systems, 2003, 20(2):45-63.
Hawkes, E. et al., A Soft Robot that Navigates its Environment Through Growth, Science Robotics, 2017, 2(8):eaan3028, pp. 1-7.
Hu, W. et al., Small-Scale Soft-Bodied Robot with Multimodal Locomotion, Nature, 2018, 554(7690):81-85.
Hyatt, P. et al., Configuration Estimation for Accurate Position Control of Large-Scale Soft Robots, IEEE/ASME Transactions on Mechatronics, 2018, 24(1):88-99.
Ilievski, F. et al., Soft Robotics for Chemists, Angew. Chem. Int. Ed., 2011, 50:1890-1895.
Klein, E. et al., Task Group 142 Report: Quality Assurance of Medical Accelerators, Medical Physics, 2009, 36(9):4197-4212.
Larsson, B., Pre-Therapeutic Physical Experiments with High Energy Protons, British Journal of Radiology, 1961, 34(399):143-151.
Lawrence, J., Proton Irradiation of the Pituitary, Cancer, 1957, 10(4):795-798.
Li, S. et al., Fluid-Driven Origami-Inspired Artificial Muscles, Proceedings of the National Academy of Sciences, 2017, 114(50):13132-13137.
Li, S. et al., A Vacuum-Driven Origami "Magic-Ball" Soft Gripper, 2019 IEEE International Conference on Robotics and Automation, 2019, pp. 7401-7408.
Li, S. et al., Tension Pistons: Amplifying Piston Force Using Fluid-Induced Tension in Flexible Materials, Advanced Functional Materials, 2019, 29(30), 22 pages.
Lin, H. et al., GoQBot: A Caterpillar-Inspired Soft-Bodied Rolling Robot, Bioinspiration & Biomimetics, 2011, 6(2):026007, 14 pages.
Liu, X. et al., Optimization Based Trajectory Planning for Real-Time 6DoF Robotic Patient Motion Compensation Systems, PloS ONE, 2019, 14(1):e0210385, 16 pages.
Miriyev, A. et al., Soft Material for Soft Actuators, Nature Communications, 2017, 8:596, pp. 1-8.
Miura, K., Method of Packaging and Deployment of Large Membranes in Space, The Institute of Space and Astronautical Science, Report No. 618, Dec. 1985, pp. 1-9.
Miyashita, S. et al., Ingestible, Controllable, and Degradable Origami Robot for Patching Stomach wounds, In 2016 IEEE International Conference on Robotics and Automation (ICRA), 2016, 8 pages.
Munzenrider, J. et al., Proton Therapy at Harvard, Strahlentherapie, 1985, 161(12):756-763.
Nelson, B. et al., Microrobots for Minimally Invasive Medicine, Annual Review of Biomedical Engineering, 2010, 12:55-85.
Rich, S. et al., Untethered Soft Robotics, Nature Electronics, 2018, 1(2):102-112.
Robertson, M. et al., New Soft Robots Really Suck: Vacuum Powered Systems Empower Diverse Capabilities, Science Robotics, 2017, 2(9):eaan6357, 27 pages.

(56) References Cited

OTHER PUBLICATIONS

Roche, E. et al., Soft Robotic Sleeve Supports Heart Function, Science Translational Medicine, 2017, 9(373):aaf3925, 34 pages.
Runciman, M. et al., Soft Robotics in Minimally Invasive Surgery, Soft Robotics, 2019, 6(4):423-443.
Rus, D. et al., Design, Fabrication and Control of Soft Robots, Nature, 2015, 521(7553):467-475.
Rutherford, E., Collision of a Particles with Light Atoms. IV. An Anomalous Effect in Nitrogen, Philosophical Magazine, 2010, 90(S1):31-37.
Sanan, S. et al., Physical Human Interaction for an Inflatable Manipulator, In 2011 Annual International Conference of the IEEE Engineering in Medicine and Biology Society, 2011, pp. 7401-7404.
Savitzky, A. et al. Smoothing and Differentiation of Data by Simplified Least Squares Procedures, Analytical Chemistry, 1964, 36(8):1627-1639.
Schenk, M. et al., Geometry of Miura-folded Metamaterials, PNAS, 2013, 110(9):3276-3281.
Shepherd, R. et al., Multigait Soft Robot, PNAS, 2011, 108(51):20400-20403.
Shintake, J. et al., Soft Robotic Grippers, Advanced Materials, 2018, 30(29):1707035, pp. 1-33.
Stewart, D., A Platform with Six Degrees of Freedom, Proceedings of the Institution of Mechanical Engineers, 1965, 180(1):371-386.
Stewart, D., A Platform with Six Degrees of Freedom, Aircraft Engineering and Aerospace Technology, 1966, 38(4):30-35.
Takeichi, M. et al., Development of Giacometti Arm with Balloon Body, IEEE Robotics and Automation Letters, 2017, 2(2):951-957.
Tolley, M. et al., A Resilient, Untethered Soft Robot, Soft Robotics, 2014, 1(3):213-223.
Miura, K. et al., Synthesis of Rigid-Foldable Cylindrical Polyhedra, Symmetry: Art and Science, 2010, pp. 204-213.
Nakase, Y. et al., A Novel Procedure for Introducing Large Sheet-Type Surgical Material with a Self-Expanding Origami Structure Using a Slim Trocar (Chevron Pleats Procedure), Surgical Endoscopy, 2017, 31:3749-3754.
Wilson, R., Radiological Use of Fast Protons, Radiology, 1946, 47(5):487-491.
World Health Organization, Cancer, https://www.who.int/news-room/fact-sheets/detail/cancer/, Feb. 3, 2022, 7 pages.
Yan, S. et al., Reassessment of the Necessity of the Proton Gantry: Analysis of Beam Orientations from 4332 Treatments at the Massachusetts General Hospital Proton Center Over the Past 10 Years, International Journal of Radiation Oncology Biology Physics, 2016, 95(1):224-233.
Yang, D. et al., Buckling Pneumatic Linear Actuators Inspired by Muscle, Advanced Materials Technologies, 2016, 1(3):1600055, pp. 1-6.
Yim, M. et al., Modular Self-Reconfigurable robot Systems, IEEE Robotics & Automation Magazine, 2007, pp. 43-52.
Zhang, Y. et al., Design and Kinematic Analysis of Positioning Chair for Proton Heavy Ion Radiotherapy, In BIBE 2018; International Conference on Biological Information and Biomedical Engineering, pp. 1-5. VDE, 2018.
PCT International Search Report and Written Opinion, PCT/US2020/062946, Feb. 26, 2021, 12 pages.
European Patent Office, Extended Search Report, Application No. 20896618.4, Dec. 5, 2023, 8 pages.
Notice of First Office Action in Chinese Application No. 202080095330.7; received on Apr. 28, 2025.

* cited by examiner

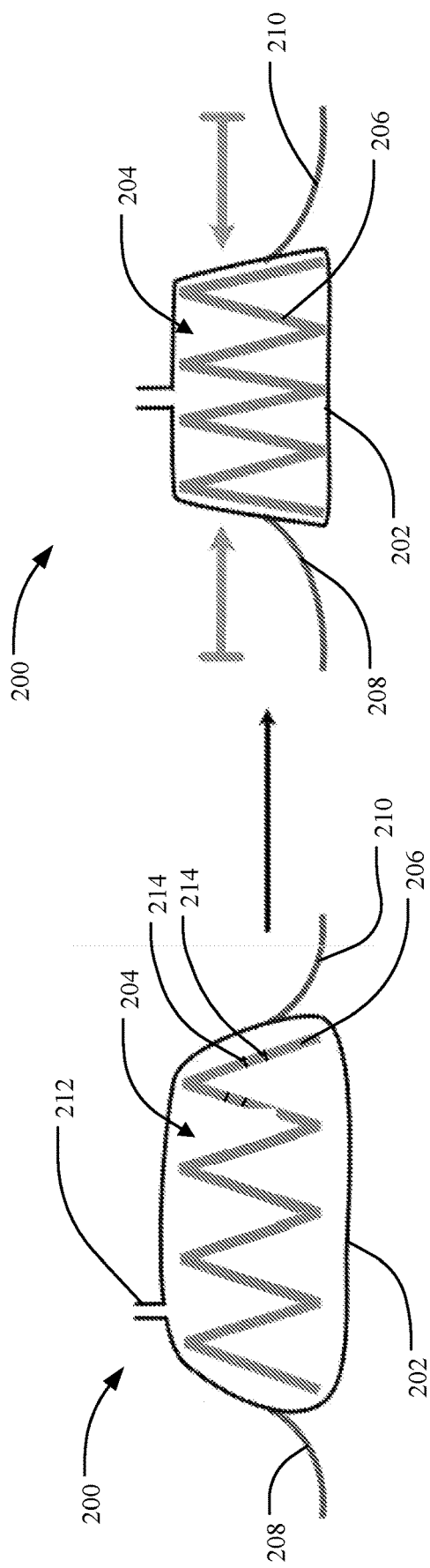
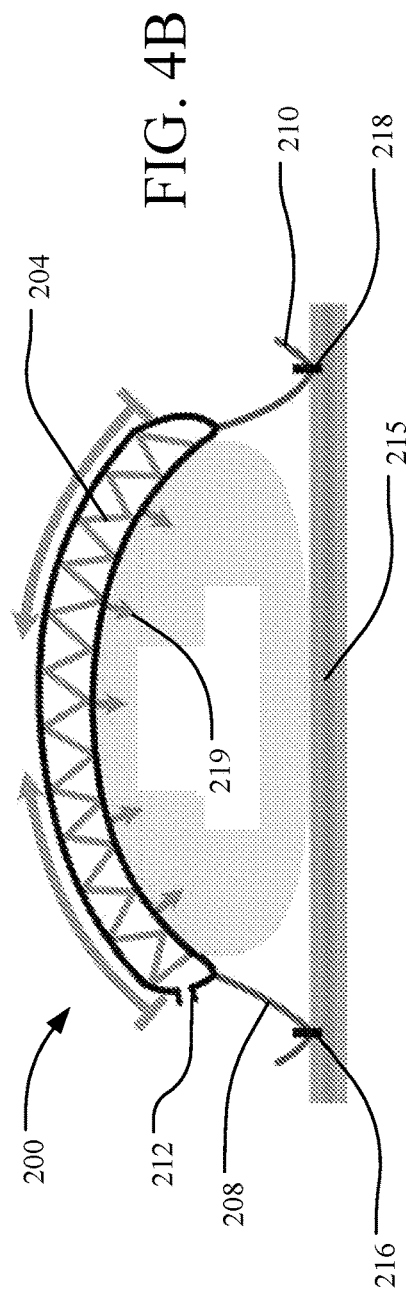
FIG. 4A
FIG. 4B

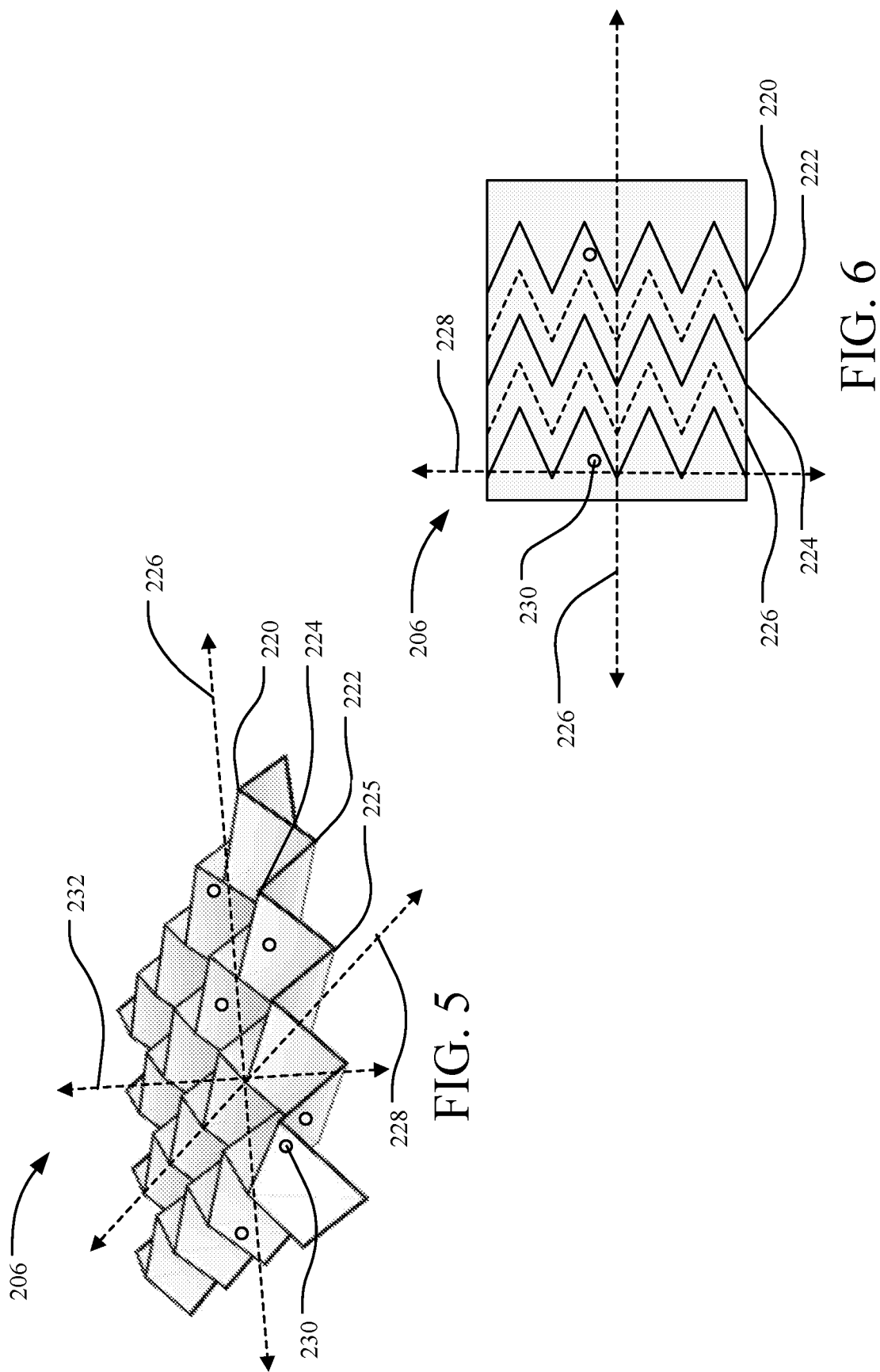

SYSTEMS AND METHODS FOR PATIENT POSITIONING DURING RADIOTHERAPY

CROSS-REFERENCE TO RELATED APPLICATIONS

This application represents the United States national stage entry of PCT International Application No. PCT/US2020/062946 filed Dec. 2, 2020, and entitled "Systems and Methods for Patient Positioning During Radiotherapy" which claims priority to U.S. Patent Application No. 62/942,418 filed Dec. 2, 2019, and entitled, "Robot Systems for Compact Proton Therapy System," the contents of each of which are hereby incorporated by reference in their entirety.

STATEMENT REGARDING FEDERALLY SPONSORED RESEARCH

N/A.

BACKGROUND

Radiation therapy is a form of oncological treatment using radiation to directly or indirectly (e.g., through oxygen radicals) damage the deoxyribonucleic acid ("DNA") of tumor cells, thereby destroying the tumor cells or inhibiting their ability to reproduce. Radiation therapy includes using photons (e.g., X-rays) to deliver the radiation and also the use of particles (e.g., protons, electrons, etc.) to deliver the radiation therapy. Generally, particle radiation therapy is considered as the most advanced and precise form of radiation therapy. In proton radiation therapy, for example, the proton beam traveling through matter deposits most of its energy right before it stops, which is characterized by a peak in a plot of energy loss of ionizing radiation traveling through matter referred to as the Bragg peak. Thus, particle radiation therapy, as compared to conventional photon radiation therapy, can provide a reduced radiation dosage to healthy tissue (e.g., reducing side effects), while increasing the radiation dosage to the tumor tissue.

While there can be considerable advantages to particle radiation therapy, currently less than 1% of all patients who receive radiation therapy get proton therapy. Some reasons for this discrepancy can be attributed to the high capital cost needed and the large spatial footprint required for the treatment system. For example, the typical size of a state-of-the-art proton therapy system ranges from 200 $m^2$ to 600 $m^2$ with a height of about 12 m—a size considerably larger than other more traditional photon based radiation therapy systems. As the size and cost of these proton radiation therapy systems (and other particle based systems) decreases, more patients can be provided with particle based radiation therapy.

Furthermore, implanting a proper or ideal particle radiation therapy plan is complicated and requires extensive manual resources. For example, particle radiation therapy systems utilize fixed sources relative to which the patient must be precisely positioned. That is, properly utilizing the Bragg peak requires that the patient be positioned very precisely to ensure that the charged particles arrive in the tumor just as the particle experiences the Bragg peak. This requires careful planning, but then substantial manual efforts to ensure that the patient is properly positioned.

The comparative lack of precision required in photon radiation therapy allows for the use of a radiation source that can be moved about the patient and even the use of patient beds can move and be adjusted. That is, photon radiation therapy does not employ a Bragg peak that necessitates the precise delivery of an individual particle into the tumor. Given the comparative lack of precision required and in an effort to limit the undesired irradiation of healthy tissue, systems have been developed that move the radiation source about the patient and even adjust the position of the patient bed relative to the radiation source to allow the beam to be delivered along a variety of different angles during the photon radiation therapy process. By moving the position of the beam relative to the patient, the dose of radiation received by healthy tissue aligned along one delivery position for the photon radiation beam can be reduced.

Unfortunately, in particle radiation therapy, patient movement, even subtle movements, can be particularly problematic because patient movement can result in the particle experiencing the Bragg peak in an improper or undesirable location. As such, patients are often positioned on a fixed patient bed and immobilized using straps that are locked in place to immobilize the patient in a fixed position for the entire radiotherapy process. Though the strategic use of the Bragg peak helps to control the damage to healthy tissue, it does not ameliorate it.

Regardless of whether or not radiation therapy is particle or photon based, it would be desirable to have improved systems and methods for controlling undesired radiation doses and ensuring careful implementation of a radiation therapy plan.

SUMMARY OF THE DISCLOSURE

The present disclosure overcomes the aforementioned drawbacks by providing systems and methods for patient positioning, patient immobilization, and patient repositioning during a radiation therapy process. Some aspects of the disclosure provides systems and methods for delivering radiotherapy to a patient that can be computer controlled and automated to ensure proper patient immobilization, and patient repositioning, even as the patient is repositioned using an adjustable or controllable patient support system during the radiation therapy process, and even when the radiation therapy is a particle radiation therapy.

In accordance with one aspect of the present disclosure, a system is provided for delivering radiotherapy to a patient. The system includes a patient support structure configured to receive a patient during a radiotherapy process using a radiotherapy source to deliver a therapy to the patient when positioned on the patient support structure. The system also includes a patient positioning system configured to adjust a position of the patient support structure relative to the radiotherapy source, and a flexible actuator configured to secure the patient to the patient support and adjust a position of at least the portion of the patient relative to the patient support. The system further includes an imaging system configured to acquire imaging data of the patient, the patient support, and the flexible actuator during the radiotherapy process and a computer system. The computer system is configured to control adjustment of the flexible actuator in at least one dimension and receive the imaging data and direct the patient positioning system to adjust the position of the patient support structure during the radiotherapy process and direct the flexible actuator to immobilize the patient as the patient positioning system adjusts the position of the patient support structure and reposition at least a portion of the patient relative to a radiotherapy plan.

In accordance with another aspect of the present disclosure, a system is provided for delivering radiotherapy to a patient that includes a radiotherapy source configured to deliver radiotherapy using a fixed beam to a patient during a radiotherapy process. The system also includes a patient support structure configured to receive the patient during the radiotherapy process, a patient positioning system configured to adjust a position of the patient support structure relative to the radiotherapy source, and a flexible actuator configured to secure the patient to the patient support and adjust a position of at least a portion of the patient relative to the patient support. The system further includes an imaging system configured to acquire imaging data of the patient, the patient support, and the flexible actuator during the radiotherapy process and a computer system. The computer system is configured to control adjustment of the flexible actuator in at least one dimension and receive the imaging data and direct the patient positioning system to adjust the position of the patient support structure during the radiotherapy process and direct the flexible actuator to immobilize the patient as the patient positioning system adjusts the position of the patient support structure and reposition at least a portion of the patient relative to a radiotherapy plan.

In accordance with yet another aspect of the present disclosure, a method is provided for restraining and repositioning a patient during a radiotherapy procedure. The method includes determining a current position of a patient on a patient support, wherein the patient is positioned to receive radiotherapy from a radiotherapy source during a radiotherapy process following a radiotherapy plan that includes a relative position of the patient to the radiotherapy source. The method also includes repositioning the patient during the radiotherapy process using a patient positioning system configured to adjust a position of the patient support structure relative to the radiotherapy source and controlling a flexible actuator that secures the patient to the patient support and adjust a position of the patient relative to the patient support using the flexible actuator to adjust at least a portion of the patient in at least one dimension. The method further includes acquiring imaging data of the patient, the patient support, and the flexible actuator during the radiotherapy process. The method further includes analyzing the imaging data relative to the radiotherapy plan to determine an updated position of the patient relative to the radiotherapy plan and repositioning the patient using the flexible actuator to match a further updated position of the patient with the radiotherapy plan.

The foregoing and other aspects and advantages of the present disclosure will appear from the following description. In the description, reference is made to the accompanying drawings that form a part hereof, and in which there is shown by way of illustration one or more exemplary versions. These versions do not necessarily represent the full scope of the disclosure.

BRIEF DESCRIPTION OF THE DRAWINGS

The following drawings are provided to help illustrate various features of non-limiting examples of the disclosure, and are not intended to limit the scope of the disclosure or exclude alternative implementations.

FIG. 4A is a cross-sectional view of a flexible actuator of the present disclosure being adjusted between a partially-expanded position and a contracted position.

FIG. 4B is a cross-sectional view of a flexible actuator of the present disclosure deployed relative to a patient.

FIG. 5 is an isometric view of one non-limiting example of a scaffold of a flexible actuator of the present disclosure.

FIG. 6 is a top view of the scaffold of the flexible actuator of FIG. 5.

DETAILED DESCRIPTION OF THE PRESENT DISCLOSURE

Figure 1:
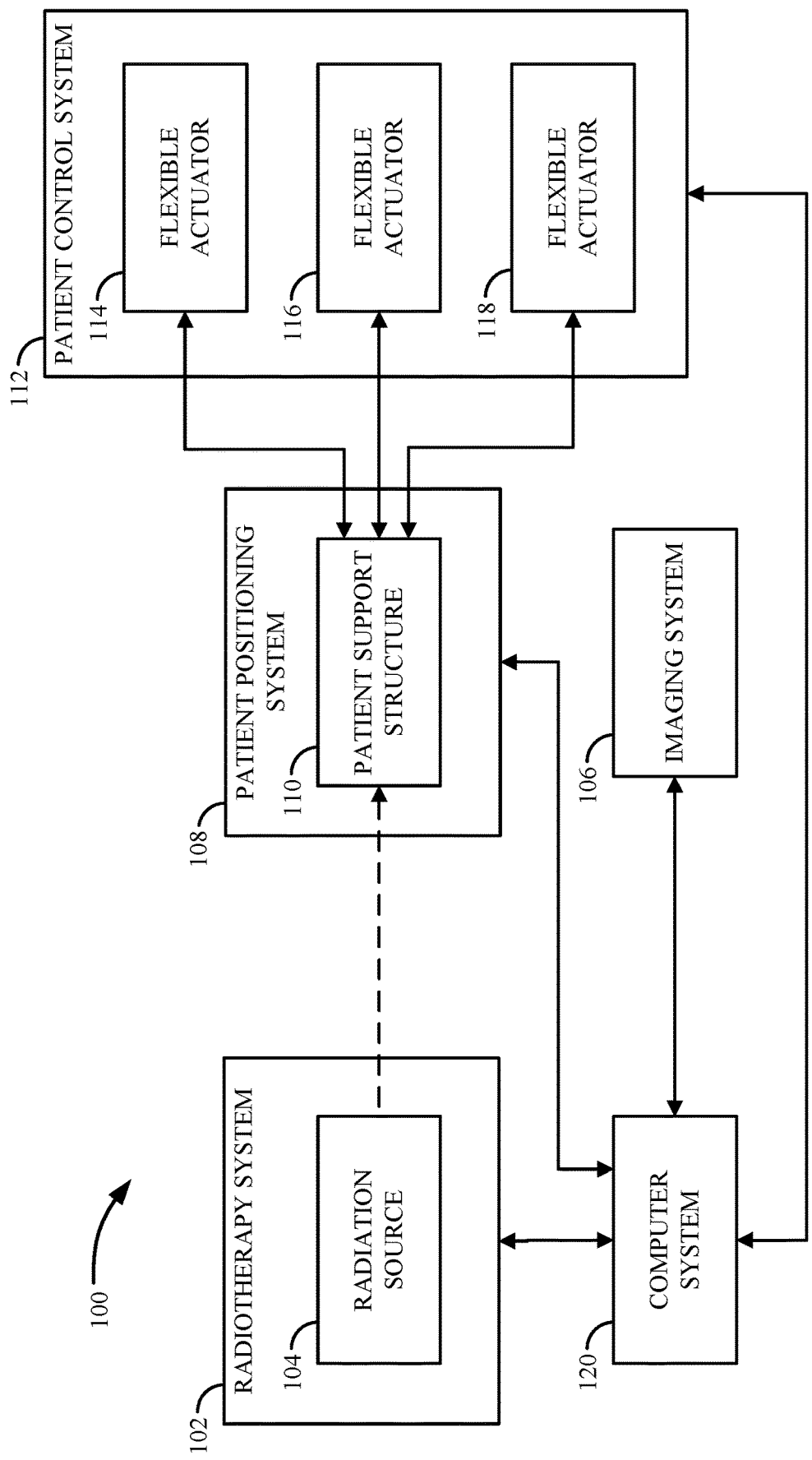
FIG. 1 is a block diagram providing a schematic illustration of a radiation therapy system in accordance with the present disclosure.

Radiation therapy (radiotherapy), which includes both photon radiation therapy and particle radiation therapy, is an essential tool in modern healthcare. However, as described above, the effectiveness of these tools can vary based on how well a clinician can manage the limitations and constraints of each system.

In addition to the practical challenges of implementing a particle radiation therapy plan effectively, it is important to note that the accessibility of proton based radiation therapy is limited for a significant number of patients, even though such patients would likely benefit from proton based radiation therapy. To increase the accessibility of proton therapy, the cost or size of proton therapy systems needs to decrease. Regarding size, one solution aims to fit a proton therapy system into a conventional radiation treatment room, which is about 50 m$^2$ with a height of 3 m. Building such a compact proton therapy system, which fits in a conventional treatment room would enable many more hospitals to supply proton treatment to patients. However, it is challenging to shrink a proton therapy system so dramatically from over 200 m$^2$ (height=12 m) to 50 m$^2$ (height=3 m), due to the properties of the particle beam (e.g., the Bragg peak), positioning a radiotherapy target relative to the particle beam needs to be done and maintained to a high level of positioning accuracy, which is typically within 1 mm and 0.5° of a target site (e.g., the tumor). This is especially difficult considering the relatively small spatial footprint, Components that must fit into the space include a proton accelerator, a proton beam-line and scanning nozzle, positioning and immobilization systems, an imaging system (choices of X-ray, magnetic resonance imaging ("MRI"), surface imaging, optical imaging (e.g., using cameras), etc.).

One way to decrease the footprint and cost of the particle therapy system is remove the traditional gantry. For example, instead of using a 100 ton proton gantry that bends the beam around the patient to allow for slightly different directions of beam incidence, a horizontal fixed proton beam line can be used for treatment, where rather than moving the source, the patient is moved relative to the fixed beam or the beam position is adjusted. While removal of the gantry frees up considerable space, removing the gantry also requires an increased emphasis on patient positioning and immobilization. For example, because the patient might be moved to different positions (e.g., according to a radiation treatment plan) with the gantry-less system (e.g., the fixed beam), it is critical that regardless of the positions, the target(s) in the patient is positioned and immobilized relative to the radiation source properly. For example, the patient needs to be immobilized reliably and moved very precisely to different positions including, for example, a sitting position, a reclined position, and a lying position.

Some conventional approaches regarding immobilization generally are not translatable to radiation therapy and thus do not address this issue. For example, seat-belts in cars and other vehicles can secure a patient to a seat, but the patient is still able to slouch, or move relative to the seat. As such, seat belts do not provide adequate securement for radiation therapy. Other conventional approaches including thermoplastic masks, and vacuum bags have been typically used during the lying position of a patient. For example, in the lying position the patient can be secured using a personalized thermoplastic mask, a modified Gill-Thomas-Cosman frame for treatment of the brain, or a vacuum bag for immobilization. While these devices may appropriately secure the patient when the patient is lying, these devices are inadequate and largely non-translatable for other patient positions (e.g., sitting, or reclined positions), or in moving between different positions. For example, these devices are not sufficiently flexible and adaptable for other positions, other than lying positions. In fact, the thermal plastic mask and vacuum bag are personalized molds for each patient that are made for a single treatment position. Thus, because many radiation treatment plans require the patient be in multiple different orientations, especially those that are implemented using a fixed beam radiation system, there must be multiple of these devices, one for each different position. For example, multiple thermal plastic masks and vacuum bean bags need to be made and stored for each different position. Such a configuration has disadvantages. First, on each day of treatment, patients would need to be re-positioned by changing to a different set of immobilization devices, which adds additional time and complexity issues (e.g., prone to errors). Second, if there are changes to the patient's body shape during the treatment period which ranges from 1 day to 35 days, the conventional immobilization device may need to be re-molded to the new body shape.

Some non-limiting examples of the disclosure provide advantages to these issues (and others) by providing improved systems and methods for patient positioning during radiation therapy. For example, some non-limiting examples of the disclosure provide a patient support structure that supports a patient, a system for adjusting the patient support structure, and a system that can secure the patient to the patient support and reposition the patient after movement, whether by the patient or caused by movement of the patient support structure. The system can include a number of flexible actuators that can be actuatable in at least two actuation directions (or ins some cases at least one actuation direction), and that each secure a portion of the patient by having opposing portions (e.g., ends) of each flexible actuator being coupled to the support structure. Each of these flexible actuators can secure a different portion of the patient to the patient support structure. For example, a first flexible actuator can support one shoulder of the patient, a second flexible actuator can support the opposing shoulder of the patient, and a third flexible actuator can support a waist (or groin) of the patient. A fluid source can be in communication with an internal volume of a flexible actuator to drive actuation of the flexible actuator.

In some non-limiting examples, an increasing actuation force provided to a given flexible actuator provides at least three advantages. First, the increase in actuation force itself secures that portion more snuggly to the patient support structure. Second, the increase in actuation force provides a tactile response to the patient thereby improving the focus of the patient, which can secure the patient by the patient flexing a desired muscle to hold that position. Thus, the flexible actuators can help prevent the patient from slouching due to gravitational pull and relaxing (e.g., due to lack of focus). Third, the multi-directional movement of the flexible actuator can be used to reposition the patient as well as, in some cases, the target inside the patient relative to other organs.

FIG. 1 is a schematic illustration of a radiation therapy system 100 in accordance with the present disclosure. The radiation therapy system 100 can include a radiotherapy system 102 having a radiation source 104, an imaging system 106, a patient positioning system 108 having a patient support structure 110, a patient control system 112 having flexible actuators 114, 116, 118, and a computer system 120. The radiotherapy system 102 can be implemented in different ways. For example, the radiotherapy system 102 can include a rotatable gantry implemented as a cylinder gantry, a ring gantry, a C-arm gantry, etc., that is pivotable about one or more rotational axes. As another example, the radiotherapy system 102 can be implemented to include a robotic arm that has the radiation source 104 coupled thereto. In this case, the robotic arm and move the radiation source 104 to different locations and orientations. As yet another example, the radiotherapy system 102 can be implemented as a gantry-less radiotherapy system, in which the radiation source 104 produces a fixed radiation beam (e.g., a proton beam). In this case, the gantry-less radiotherapy system can include other components such as a particle accelerator (e.g., a cyclotron, a synchrotron, a linear accelerator ("LINAC"), etc.), a particle beamline nozzle (e.g., that emits the radiation particle beam), and radiation particle beam adjusting components to shape the trajectory of the radiation particle beam, which can include selectively activated magnets.

In some non-limiting examples, the radiation source 104 can be implemented in different ways, depending on the particular implementation of the radiotherapy system 102. For example, the radiation source 104 can be a photon based radiation beam former, such as an X-ray beam forming assembling configured to emit X-rays (e.g., an X-ray beam). In other cases, the radiation source 104 can be a LINAC configured to emit a (charged) particle radiation beam (e.g., electrons, protons, etc.), such as, for example, when the radiotherapy system 102 is implemented as including a robot arm having the radiation source 104 coupled thereto. In still other cases, such as when the radiotherapy system 102 is implemented as a gantry-less radiotherapy system, the radiation source 104 can include one or more charged particle accelerators (e.g., a LINAC, a cyclotron, etc.), and can include a beamline nozzle configured to direct a radiation particle beam (e.g., a proton radiation beam). In this case, the radiation source 104 can include other beam directing and focusing components, such as radiation particle beam bending magnets, and radiation particle beam focusing magnets. In some cases, these magnets can be electromagnets that can be selectively activatable by the computer system 120.

In some non-limiting examples, the radiation therapy system 100 can include an imaging system 106 that can be configured to acquire imaging data of the patient, the patient support, and the patient control system 112 (including the flexible actuators 114, 116, 118). For example, when the patient is positioned on and secured to the patient support structure 110 by the flexible actuators 114, 116, 118, the imaging system 106 is configured to acquire imaging data that includes the patient, the patient support structure 110, the patient control system 112 including each of the flexible actuators 114, 116, 118. In some cases, the imaging data acquired by the imaging system 106 can be two-dimensional ("2D") imaging data, or three-dimensional ("3D") imaging data.

The imaging system 106 can be implemented in different ways. For example, the imaging system 106 can be implemented as a medical imaging system, such as an X-ray or fluoroscopy system. However, the imaging system 106 may be any of a variety of imaging modalities or combinations of imaging modalities, such as a computed-tomography ("CT") imaging system (e.g., a C-arm CT system), a magnetic resonance imaging ("MRI") imaging system, a positron emission tomography ("PET") imaging system, etc. In other cases, the imaging system 106 can be an optical based imaging system including one or more imaging sensors (e.g., charge coupled devices ("CCD") imaging sensors, complementary metal oxide semiconductor ("CMOS") imaging sensors, etc.). In particular, the imaging system 106 can include one camera, or two cameras (e.g., in a stereoscopic configuration), etc. Irrespective of the imaging modality, the imaging system 106 can use a number of imaging markers (e.g., imaging fiducials) that can be placed on a patient, such as, for example, on one or more of the flexible actuators 114, 116, 118 and used by the imaging system 106, as appropriate, to track the position of the markers relative to the portion of the subject that the marker is coupled to. As shown, the computer system 120 is in communication with the imaging system 106.

The patient positioning system 108 that includes the patient support structure 110 can be implemented in different ways. For example, the patient support structure 110 can be a device that resembles a chair that supports the patient when the patient is seated in the chair position. In this case, for example, the chair can be one or more portions of the chair can be actuatable relative to other portions of the chair. For example, the back (or the seat) can pivot relative to the seat (or back). In other cases, the chair is a rigid structure that can be moved by the patient positioning system 108. In other cases, the patient support structure 110 can be a table in which the patient is supported when the patient is in lying down position. In some cases, the patient positioning system 108 can move the patient support structure 110 in three or more degrees of freedom (e.g., six degrees of freedom). For example, the patient positioning system 108 can include a number of robotic linkages (e.g., arms coupled to an actuator) that can collectively move the patient support structure 110 to different locations and orientations. In some cases, sensors (e.g., encoders) of the patient positioning system 108 can sense the collective position of the support structure 110, which can be utilized by the computer system 120. As shown, the computer system 120 is in communication with the patient positioning system 108. Thus, the computer system 120 can sense the current position (and orientation) of the patient support structure 110, and can relate this position to the patient (e.g., registering the coordinate system of the patient positioning system 108 with the coordinate system of the imaging system 106).

In some configurations, the computer system 120 can also cause the patient positioning system 108 to move the patient support structure 110 to different positions (and orientations) as desired, such as according to a radiation treatment plan. For example, such as when the patient support structure 110 is a chair, the computer system 120 can cause the patient positioning system 108 to move the patient into a different position, such as a sitting position, a reclined position (e.g., by partially actuating and thereby pivoting a back portion of the chair relative to the seat of the chair), or a laying down position (e.g., by fully actuating and thereby pivoting the pack portion of the chair until the back portion of the chair is substantially (e.g., deviating by less than ±10%) coplanar with the seat of the chair).

In some configurations, the patient control system 112 secures the patient to the patient support structure 110, and can provide a dynamically adjustable securement forces to particular portions of the patient. In this way and as will be described, the patient control system 112 achieves both patient immobilization and patient positioning or repositioning. For example, each of the flexible actuators 114, 116, 118 can secure different portions of the patient to the patient support structure 110. In particular, opposing ends of each of the flexible actuators 114, 116, 118 can be secured to the patient support structure 110, with at least a portion (e.g., a body) of each of the flexible actuators 114, 116, 118 encapsulating a corresponding portion of the patient. In some cases, the flexible actuator 114 can secure a first body part (e.g., a shoulder), the flexible actuator 116 can secure a second body part (e.g., the other shoulder) different than the first body part, and the flexible actuator 118 can secure a third body part (e.g., the waist) that is different than the first or second body parts. In other cases, however, some of the flexible actuators 114, 116, 118 can partially overlap or can entirely overlap (or substantially entirely overlap) with each other. In this way, the overlapping flexible actuators can provide a higher amount of securement to the overlapping location.

Each of the flexible actuators 114, 116, 118 when actuated, can be compressed in two dimensions (e.g., along the x-axis and along the y-axis, within a plane, etc.), while expanded in the opposite third dimension (e.g., along the z-axis, along a direction normal to the plane, etc.). In some non-limiting examples, when the actuation is released, each of the flexible actuators 114, 116, 118 can be expanded in the two dimensions, while retracting in the opposite third dimension. In this way, the forces provided by the flexible actuators 114, 116, 118 can be better distributed about the particular portion encapsulated by the respective flexible actuators 114, 116, 118. In some cases, each of the flexible actuators 114, 116, 118 can include a sealed enclosure, a scaffold that is flexible and ridged (e.g., that bends along bend lines) located within the sealed enclosure, a port in fluid communication with the sealed enclosure, a conduit coupled to the port and in fluid communication with the sealed enclosure, and a pump coupled to the conduit. The pump, when activated (e.g., by the computer system 120), can draw fluid (e.g., air) out of the sealed enclosure thereby causing the respective flexible actuator to be actuated. The amount of fluid that is located within a given flexible actuator is related (e.g., proportional) to the pressure within the given flexible actuator. Thus, for each flexible actuator 114, 116, 118 a pressure sensor can be in fluid communication with the internal volume of the respective flexible actuator 114, 116, 118, each of which can be in communication with the computer system 120. Thus, the computer system 120 can determine the current actuation force for each flexible actuator 114, 116, 118 (e.g., to determine if the computer system 120 should adjust the force of a flexible actuator). In some cases, the scaffold of each of the flexible actuators 114, 116, 118 can be perforated or can include holes to allow better fluid communication between layers. In some cases, the scaffold of each of the flexible actuators 114, 116, 118 can have a 2D folding pattern (e.g., a Miura folding pattern, a series of folds that extend within a plane), which can allow for the contraction within the plane of the scaffold and expansion in the third dimension. In other cases, the scaffold of each of the flexible actuators 114, 116, 118 can have a 3D folding pattern (e.g., a series of folds that extend within a plane and in the remaining dimension normal to the plane).

In some non-limiting examples, such as based on a current patient position according to a radiation treatment plan, the computer system 120 can selectively adjust the actuation force of one or more of the flexible actuators 114, 116, 118 (e.g., by removing fluid, or by allowing or forcing fluid into the flexible actuator, via the pump). In this way, the patient can be more secured (e.g., restricted) by the flexible actuators from the additional force itself, while providing a tactile feedback to the patient that indicates the patient refocus and flex particular muscles (e.g., that are near the flexible actuators). Additionally, in some cases, orchestrating the actuation force of the one or more flexible actuators 114, 116, 118 by the computer system 120 can adjust the positioning of the patient or the position of the target inside the patient relative to other organs, including internal positioning and restriction of organs. For example, when one flexible actuator is situated on the waist of the subject and a second flexible actuation is situated on the chest (or shoulder) of a patient, actuation of both flexible actuators can move an organ, such as the liver downwardly, and can secure the organ more in place as compared to without the flexible actuators.

In some non-limiting examples, each of the flexible actuators 114, 116, 118, for a given compression force, can have a uniform thickness, which is desirable at least because if a radiation beam passes through a region of the flexible actuator, the radiation provided to the region is uniform. In other words, the radiation delivered to a particular region from a radiation beam passing through the uniform thickness flexible actuator is thus not dependent on the thickness of the flexible actuator.

Although the patient control system 112 has been described with three flexible actuators 114, 116, 118, fewer numbers of flexible actuators can be used, such as one, or two, while in other cases, greater numbers of flexible actuators can be used, such as four, five, six, etc. In some non-limiting examples, the flexible actuators 114, 116, 118 can be sized in different ways, such as being as large a blanket, or as small as belt strips. In some cases, a plurality of the flexible actuators can overlap according to a pattern (e.g., bodies of the flexible actuators can overlap in a cross-cross pattern). In some cases, one or more of the flexible actuators 114, 116, 118 (or others) can be integrated within, or configured to replace, a portion of (or the entire) clothing, such as pants, a jacket, socks (or other footwear), shirts, suits (e.g., similar to a wetsuit), etc.

In some non-limiting examples, the computer system 120 can be implemented in different ways. For example, the computer system 120 can include typical components used such as a processor, memory, a display, inputs (e.g., a keyboard, a mouse, a graphical user interface, a touch-screen display, etc.), communication devices, etc. In some cases, computer system 120 can simply be implemented as a processor. The computer system 120 can communicate with other computing devices and systems. In some non-limiting examples, computer system 120 can implement some or all of the processes described below.

Figure 2:
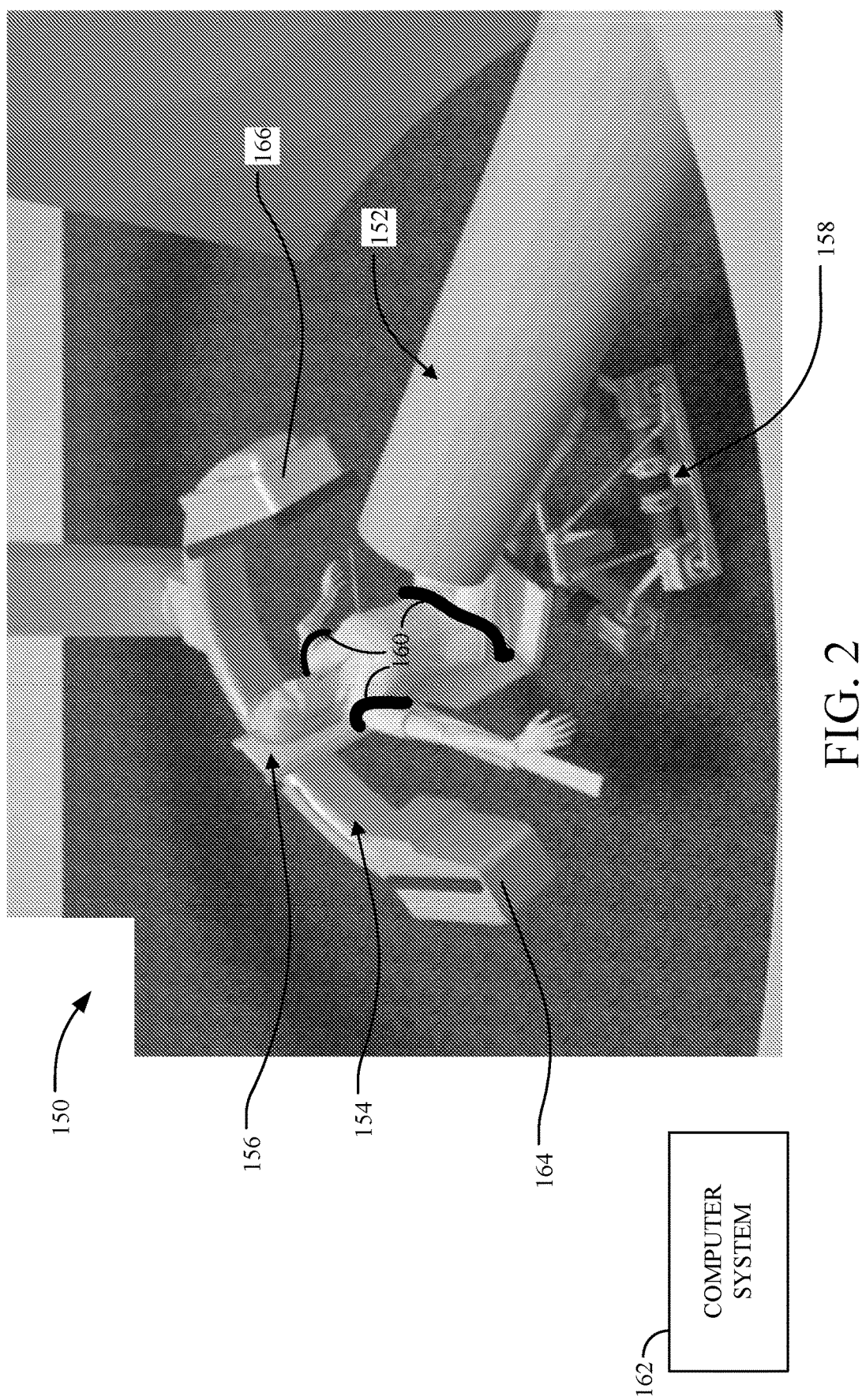
FIG. 2 is a perspective view of one non-limiting example of a radiation therapy system in accordance with the present disclosure.

FIG. 2 shows an example of a radiation therapy system 150, which is a specific implementation of the radiation therapy system 100. For example, the radiation therapy system 150 includes a radiation source 152, an imaging system 154, a patient support structure 156, a patient positioning system 158, a patient control system 160, and a computer system 162 that is in communication with the radiation source 152, the patient positioning system 158, and the patient control system 160. The radiation source 152 is implemented as a beamline nozzle configured to emit a radiation particle beam to the patient, which in this case is a proton beam. In this configuration, the radiation particle beam (e.g., the proton beam) is a fixed beam. In other words, the beamline nozzle that receives charged particles (e.g., protons) from a particle accelerator, is fixed and does not move. In some cases, the computer system 162 can adjust the trajectory of the radiation particle beam by selectively activating magnets located within the beamline nozzle. The imaging system 154 is implemented as being an X-ray imaging system, with an X-ray source 164 providing an X-ray beam through the patient and detectable by a X-ray detector 166. The imaging system 154 is shown as being a C-arm that is pivotable about one or more axes.

Figure 3:
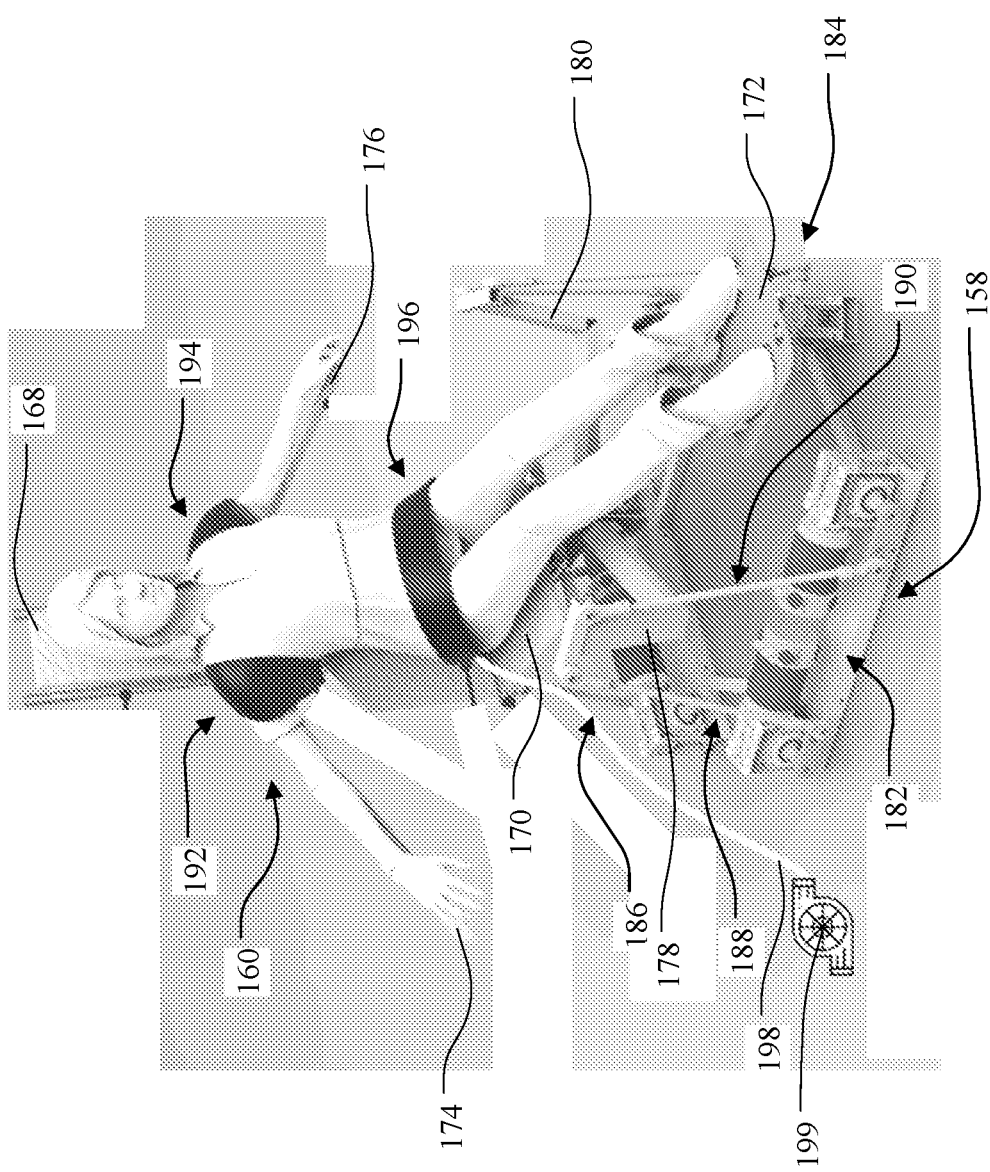
FIG. 3 is an isometric view of a patient positioned in a system in accordance with the present disclosure that includes a patient support structure, with the patient control system and positioning system of FIG. 2.

FIG. 3 shows an isometric view of a patient supported by the patient support structure 156, with the patient positioning system 158 engaged with the patient support structure 156, and with the patient control system 160 installed. The patient support structure 156 is implemented as being a chair having a backrest 168 coupled to a seat 170, and a footrest 172. The backrest 168 is configured to support the back of the patient, the seat 170 is configured to support the buttock of the patient, and the footrest 172 is configured to support the feet of the patient. Although the chair is shown as being rigid, in other configurations, portions of the chair can be moveable (e.g., actuatable to other portions of the chair). For example, the backrest 168 can be tilted backward relative to the seat 170. The chair also includes arm supports 174, 176 that each extend from different sides of the chair at an angle relative to the backrest 168. In some cases, the arm supports 174, 176 are coupled to opposing sides of the backrest 168. The arm supports 174, 176 are configured so that when arms of the patient are situated on a respective arm rest, the arms are elevated and lifted away from the sides of the patient. In some cases, such as in the illustrated non-limiting example the chair can include support beams 178, 180 that provide mounting locations for the patient positioning system 158.

As shown, the patient positioning system 158 is implemented as a robotic system that has three actuator assemblies 182, 184, 186, which can be substantially similar to each other, and thus only the actuator assembly 182 will be described in favor of brevity. The actuator assembly 182 includes pivotal linkages 188, 190 that are situated on opposing ends of the support beam 178. Each of the pivotal linkages 188, 190 can be rotatably pushed by a respective motor (e.g., an electric motor). In other words, each of the pivotal linkages 188, 190 can be rotatably coupled to both an end of the support beam 178 and a component that rotates with the motor, thereby rotatably advancing a given pivotal linkage (e.g., by adjusting its position and orientation within a plane defined by the pivotal linkage). This advancement forces the support beam 178 to adjust its orientation, thus changing the orientation of the chair. As shown, the actuator assembly 184 includes pivotal linkages rotatably coupled to the support beam 180, and the actuator assembly 186 includes pivotal linkages rotatably coupled to the chair (e.g., a guide rail). Thus, the collective positioning by the actuator assemblies 182, 184, 186 can adjust the position and orientation of the chair and thus the patient.

As shown, the patient control system 160 also includes three flexible actuators 192, 194, 196. The patient control system 160 is a specific implementation of the patient control system 112, and the flexible actuators 114, 116, 118 are specific implementations of the flexible actuators 192, 194, 196. Each of the flexible actuators 192, 194, 196 secure different portions of the patient. For example, the flexible actuator 192 has two opposing ends (or more such as four opposing ends corresponding to each edge of the flexible actuator 194) coupled to the chair and more specifically coupled to the backrest 168 of the chair, with a first shoulder of the patient encapsulated by the flexible actuator 192. The flexible actuator 194 has at least two opposing ends coupled to the chair (e.g., the backrest 168 of the chair), with a second opposing shoulder of the patient encapsulated by the flexible actuator 194. The flexible actuator 196 has at least two opposing ends coupled to the chair, with the waist (or in some cases the groin) of the patient encapsulated by the flexible actuator 196.

Each flexible actuator 192, 194, 196 can have a conduit that is in fluid communication with the internal volume of the respective flexible actuator, and can have a corresponding pump in fluid communication with the internal volume of the respective flexible actuator (e.g., via the conduit). Each pump can be controllable by the computer system 162 to pump fluid into the respective flexible actuator thereby deactuating the respective flexible actuator (e.g., to decrease the securement force provided by the flexible actuator to the respective portion of the patient), or to pump fluid out of the respective flexible actuator thereby actuating the respective flexible actuator (e.g., to increase the securement force provided by the flexible actuator to the respective portion of the patient). As shown, a conduit 198 is coupled to the flexible actuator 196 on one end and coupled to a pump 199 on an opposing end. The conduit 198 is in fluid communication with the internal volume of the flexible actuator 196. As the pump 199 is activated to draw fluid, fluid from the interior volume of the flexible actuator 196 is drawn out through the conduit 198 and out through the pump 199 to increase the actuation force provided by the flexible actuator 196, or in other words, to further constrict the portion encapsulated by the flexible actuator 196. When fluid is introduced back into the interior volume of the flexible actuator 196 (e.g., forcibly via the pump 199, or by decreasing the suction of the pump 199) the actuation force provided by the flexible actuator 196 is decreased to lessen the constriction of the portion encapsulated by the flexible actuator 196. The flexible actuators 192, 194 operate in a similar manner as the flexible actuator 196.

FIGS. 4A and 4B show various schematic illustrations of a flexible actuator 200, which can be the previously described flexible actuators. The flexible actuator 200 includes a sealed enclosure 202 that defines an internal volume 204, a scaffold 206 that is folded in at least a 2D folding pattern, connectors 208, 210 connected to opposing ends of the sealed enclosure 202, and a port 212 that is in fluid communication with the internal volume 204. The scaffold 206 can have rigid portions defined between a bend line that can fold and retract along each bend line. In some cases, the flexible actuator 200 can include perforations 214 directed through some (or each) of the rigid portions, or in other cases, the scaffold 206 can include a number of holes directed through some (or each) of the rigid portions. The holes and the perforations 214 can provide fluid communication pathways that can more easily vacate fluid out or inject fluid into the internal volume 204.

The connectors 208, 210 are illustrated as being tethers, or strips of material that extend from opposing ends of the flexible actuator 200. Each of the connectors 208, 210 can include one or more fasteners (e.g., hook and loop fasteners, threaded fasteners such as bolts, adhesives, etc.) to fasten a given connector to a patient support structure. As shown, the port 212 is in fluid communication with the internal volume 204 of the sealed enclosure. In some cases, the port 212 can provide an interface to more easily receive and couple a conduit to the flexible actuator 200.

Although the flexible actuator 200 has been illustrated with a single port 212, and two connectors 208, 210, in other configurations, more ports can be added (e.g., with corresponding conduits either connecting and in fluid communication with respective pumps or a single pump), and more connectors can be added, such as three, four, five, etc. In some cases, the sealed enclosure 202 is an elongated sheet, in which case connectors can emanate from each side of the sheet.

Referring to FIG. 4A the flexible actuator 200 is shown in a first configuration prior to actuation and then being controlled to move to a second configuration that is a contracted or actuated configuration, after fluid has vacated from the interior volume 204 thereby actuating the flexible actuator 200 (e.g., compressing the flexible actuator 200 in two dimensions that exits on a plane, while expanding the flexible actuator in the remaining dimension normal to the plane). FIG. 4B shows the flexible actuator 200 secured to a patient support structure 215 having loops 216, 218. In particular, the connector 208 is received through and is fastened to the loop 216, and the connector 210 is received through and fasted to the loop 218. In this configuration, the multi-dimensional actuation of the flexible actuator 200 delivers a precisely controlled force 219 to the patient that can be used to both immobilize and reposition the patient.

FIG. 5 shows an isometric view of the scaffold 206. The scaffold 206 is folded in a 2D folding pattern, where folds 220, 222, 224, 225 extend along the x-axis 226 and the y-axis 228 of the scaffold 206 (e.g., where the x-axis 226 and the y-axis are perpendicular to each other). In the illustrated non-limiting example the folds 220, 222, 224, 225 are zig-zag shaped, however in alternative configurations the folds 220, 222, 224, 225 can have other shapes. In particular, the 2D folding pattern is a Miura folding pattern, however in other configurations, other 2D folding patterns can be used. As shown, the scaffold 206 can include a number of holes 230 directed through the scaffold (e.g., in alternative or in addition to the perforations 214).

Referring to both FIG. 5, and FIG. 6 that shows a top view of the scaffold 206, the folding of the scaffold 206 can retract along both the x-axis 226 (e.g., by adjacent folds coming closer into connect, such as the folds 220, 222), and the y-axis 228 (e.g., with a fold, folding on itself along this direction), such as when the fluid is evacuated from the interior volume 204. Additionally, when the scaffold 206 compresses, the scaffold 206 also can expand along the z-axis 232 (e.g., where the z-axis is perpendicular to the x-axis 226 and the y-axis 228. Similarly, when fluid is introduced back into the interior volume 204 the scaffold 206 can expand along both the x-axis 226 and the y-axis 228 (e.g., by unfolding), while the scaffold 206 can retract along the z-axis 232.

Figure 7:
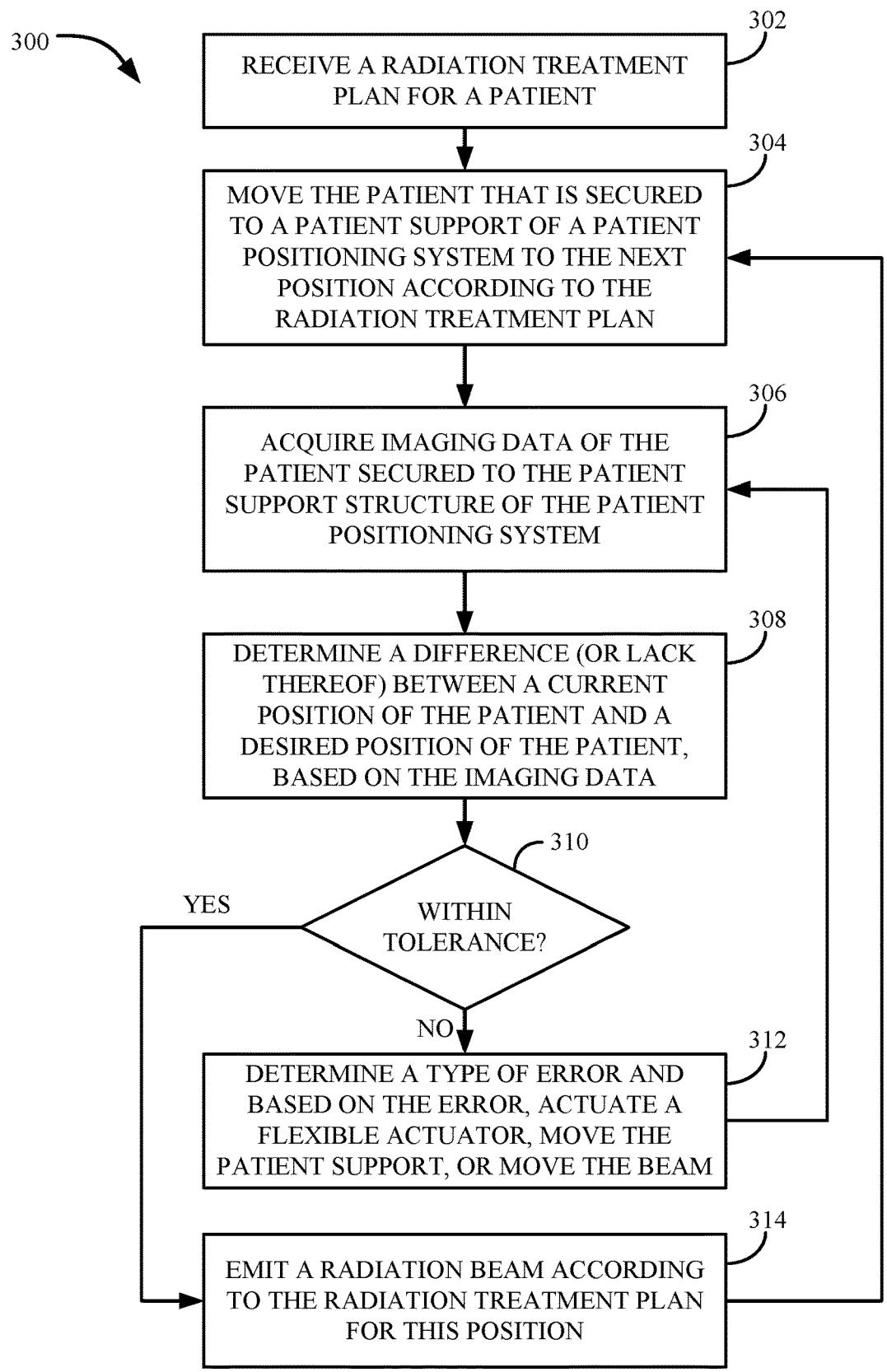
FIG. 7 is a flowchart setting forth a series of non-limiting example steps forming one non-limiting example of a process for restraining and repositioning a patient during a radiotherapy procedure in accordance with the present disclosure.

FIG. 7 shows a flowchart of a process 300 for restraining and repositioning a patient during a radiotherapy procedure, which can be implemented using the radiation therapy systems describe above. Some or all of the blocks of process 300 can be implemented, as appropriate, using one or more computing devices (e.g., the computer system 120).

At 302, the process 300 can include a computing device receiving a radiation treatment plan for a patient. In some cases, this can include receiving a number of radiation beam paths each having a desired depth, intensity, and duration. In some cases, each of the beam paths can define a corresponding different patient orientation (e.g., relative a radiation source). In some cases, each beam path (or each patient position) of the radiation treatment plan can include a corresponding target location (e.g., an internal target location) for the patient. For example, the target location can be a region of a tumor of the patient.

At 304, the process 300 can include a computing device moving the patient that is secured to a patient support of a patient positioning system to the next position according to the radiation treatment plan. For example, a computing device can cause the patient positioning system to move the patient support (and thus the patient) to the next desired patient position (and orientation). In some non-limiting examples, at 304 the process can include a computing device adjusting an actuation force of the flexible actuators of an immobilization system to secure, immobilize, restrain, or reposition the patient relative to the patient support (e.g., for the particular position according to the radiation treatment plan).

At 306, the process 300 can include a computing device acquiring imaging data (e.g., via an imaging system) of the patient secured to the patient support of the patient positioning system. In some cases, this can include a computing device determining, based on the imaging data, a current position of the patient on the patient support, which can be relative to a radiation source (e.g., a radiation particle beam). In addition to the position of the patient, this also determines the target (tumor) positions relative to the surrounding healthy tissues and their shape.

At 308, the process 300 can include a computing device determining a difference (or lack thereof) between a current position of the patient and a desired position of the patient. In some cases, each of the current position and the desired position can be relative to a radiation particle beam, imaging markers, imaging fiducials, etc.

At 310, the process 300 can include a computing device determining whether or not the patient is within a movement tolerance (e.g., 1 mm). If at 310, the computing device determines that the patient movement is within tolerance, the process 300 can proceed to block 314 of the process 300 to cause a radiation source to emit a radiation beam according to the radiation treatment plan for this radiation beam path and corresponding patient position. Once the radiation therapy beam has been provided according to the radiation treatment plan, the process 300 can proceed back at block 304 of the process 300 to move the patient to the next position according to the radiation treatment plan (e.g., if there are additional positions).

If at 310, the computing device determines that patient movement exceeds the threshold, the process 300 can proceed to block 312. At 312, the process 300 can include the computing device determining a type of error, and based on the error, repositioning the patient by one or more of adjusting the actuation of one or more of the flexible actuators, moving the patient positioning system, or moving the radiation beam (e.g., a radiation particle beam). In some non-limiting examples, this can include a computing device, based on the imaging data, determining that the error is a surface error or a skin error and based on the surface error, adjusting the actuation of the one or more flexible actuators until the surface error has been mitigated to provide a surface correction. In some non-limiting examples, this can include a computing device determining, based on the imaging data, the error is a posture error (e.g., slouching) and based on the posture error adjusting the actuation (e.g., increasing the actuation force) of the one or more flexible actuators until the posture of the patient is within an appropriate level to provide a posture correction. In some non-limiting examples, this can include the computing device, based on the imaging data, determining that the error is a beam error (or an error that can be fixed by adjusting the beam), and based on the beam error, adjusting the shape, the trajectory of the radiation beam (e.g., by selectively activating magnets when the radiation source provides a radiation particle beam).

In some non-limiting examples, such as if at 310 the computing device determines that the target location for the particular position exceeds a threshold, the computing device can adjust the actuation force of the one or more flexible actuators until a portion of the target location is in alignment with the radiation source (e.g., a fixed radiation beam, or the beam nozzle that emits the fixed radiation beam). In this way, the one or more flexible actuators can internally move the target site, which can be a portion of a tumor of an internal organ (e.g., by choreographed actuation of multiple flexible actuators).

In some cases, once the computing device determines that the require movement has been made, process 300 can proceed back to block 306 to acquire additional imaging data.

EXAMPLES

The following examples have been presented in order to further illustrate aspects of the disclosure, and are not meant to limit the scope of the disclosure in any way. The examples below are intended to be examples of the present disclosure and these (and other aspects of the disclosure) are not to be bounded by theory.

Proton therapy has a substantial physical advantage over conventional cancer radiation treatment with X-rays. Proton therapy reduces the radiation dose to healthy tissues and therefore the toxicity and side effects to the patients. However, the current high capital cost and required space make proton therapy a very limited resource. In current proton therapy, the patient is fixed on a table and a gantry is used to bend the proton beam for treatment. We propose to change the model by precisely moving an irradiation target within a patient relative to a fixed, or slightly adjustable proton beam rather than grossly moving the beam relative to the patient. This requires a robotic device to move the patient and a strong and flexible patient control device to ensure that the patient's body position remains accurate during position shifts. We introduce a solution to enable compact and affordable proton therapy using a parallel robot with real-time surface positioning feedback and a patient immobilization control system made of soft robotic actuators. Immobilization experiments with healthy volunteers demonstrate that our prototype device can position and immobilize healthy volunteers in sitting position to clinical standards and correct slouching through a feedback loop. The soft robotic patient control device is strong but soft and comfortable as well as adaptive to the body shape. The force that the patient control device can exert on the body using negative pneumatic pressure was characterized. This new patient control device and the robotic positioning system have great potential to significantly reduce the cost of proton radiation cancer treatment.

Combining several advanced technologies in robotics and control techniques provides the solution to the problem. In this study, we designed and fabricated a universal device made from soft actuators to provide strong and comfortable patient control. This soft robot device, compared to a passive non-electric device (e.g. a belt), could be controlled and its applied force could be automatically adjusted for different patients. Additionally, the actuator can be designed to fit the shape of specific body parts to optimize the coverage, therefore providing adaptable force for patient control. We used a 6-degree-of-freedom (DOF) parallel-robot-controlled chair and integrated it with surface imaging in a feedback loop to achieve a high level of precision and maneuverability of the patient between different treatment positions. More specifically, we made the soft patient control based on a fluid-driven origami-inspired artificial muscles (FOAM) concept. We evaluated the effectiveness of the system through an experiment with healthy volunteers. Our soft-actuator, patient control device can reduce the volunteers position change as well as the magnitude of the respiratory motion in some volunteers. The effectiveness of the controller integrating with the surfacing imaging on the positioning accuracy was evaluated and confirmed.

This study was designed to build on advances in proton therapy systems, soft robots, robotic chairs, and tracking and localization. We highlight recent relevant works in each of these categories.

The Harvard Cyclotron lab started to treat patients with proton beams in 1973. For decades, proton therapy has been delivered with the double scattering technique. The pencil beam scanning (PBS) technique developed in recent years provides a 3D dose modulation and therefore the radiation dose shaping potential is very high even from a single beam with high-resolution PBS delivery.

Robotic couches, 3 or 6 DOF, have been a commercial product in radiation therapy for patient positioning in lying position. A 6 DOF Stewart robotic motion correction research platform was developed to achieve 0.5 mm tracking accuracy. However, no robotic couch with real-time tracking and the ability to shift the patient to multiple orientations relative to the primary beam trajectory, has been applied in the clinic or to a compact proton therapy system.

Tumor position tracking and localization has been a widely studied topic. A previous research study has developed a close loop dynamic controller to track the tumor respiratory motion with the couch. An algorithm was used to predict the tumor centroid position, accounting for the latency in the system. The study showed a maximum tracking error of 1 mm using computer simulation of two commercial treatment couches. A recent study optimized the trajectory of motion compensation for the 6 DOF robotic patient couch using L-BFGS algorithm. The method considered mechanical and patient treatment limitations and concludes that steepest descent trajectory was the optimal solution.

In our study, the novel soft patient control is designed based on a fluid-driven origami-inspired artificial muscles (FOAM) concept. This is an easy to make and very cost-effective design. To focus the effort on developing and evaluating the soft patient control device, we used a standard 6 DOF parallel robotic base with a simple controller in this study. In addition, a chair top was integrated with this soft patient control device to achieve a clinical required position control system.

The system developed in this study is comprised of a parallel robot base, a patient chair with a soft patient control device attached to it, and an optical motion tracking system. This system was developed to allow patient control of a patient, while providing accuracy positioning of the patient.

The following design considerations were considered when developing a robotic patient positioner combined with a soft patient control device for a compact proton therapy system: (1) the patient control device needs to be (a) thin, i.e., <5 cm to allow for positioning close to the radiation beam nozzle, (b) universal and reusable for all patients, (c) comfortable for the patient, and (d) of reproducible thickness at each point and each treatment or placed outside the treatment beam path; (2) the part of the robot system that may be in the treatment beam trajectory needs to be made from materials that attenuate the beam as little as possible, e.g., carbon fiber composites; (3) the clinical standards for positional accuracy compared to a reference position must be below 1 mm and 0.5; and (4) the system needs to be easy to use.

In this study, we focused on a prototype for breast cancer treatment. The shoulder and abdominal region were chosen as the location for the patient control units to provide access to the breast region while preventing slouching motion of the patient in sitting position.

A new method of soft patient control was developed which meets the requirements of the system. The device was constructed from several individual units for different areas of the patient's body. Each unit is a fluid driven origami-inspired artificial muscle (FOAM) (FIG. 4A) with a Miura fold (FIG. 4B) actuated by negative relative air pressure. This type of actuator has been shown to have good durability, and no performance decrease over 30000 usage cycles. The Miura fold is chosen due to its in-plane contraction, ability to easily bend around an object, e.g., a shoulder, in the direction of contraction, and its robustness. Although typically used for actuation, by fixing the ends of the actuator to a base frame, thus restricting the lateral contraction, force is exerted normal to the actuator. Each unit was fabricated by folding a 0.18 mm thick Polyester film in the Miura fold pattern to form the skeleton of the actuator. The plastic film was perforated with the Miura fold pattern by a laser cutter (Universal Laser Systems, Inc.) after which it could then be folded by hand. In the next step the skin of the actuator was prepared by attaching a plastic air hose coupler. The skeleton was then sealed within a coated, airtight nylon-fabric sheet by an impulse heat sealer (American International Electric, Co.). The unit was completed by gluing connectors to both ends of the skin.

Figure 8:
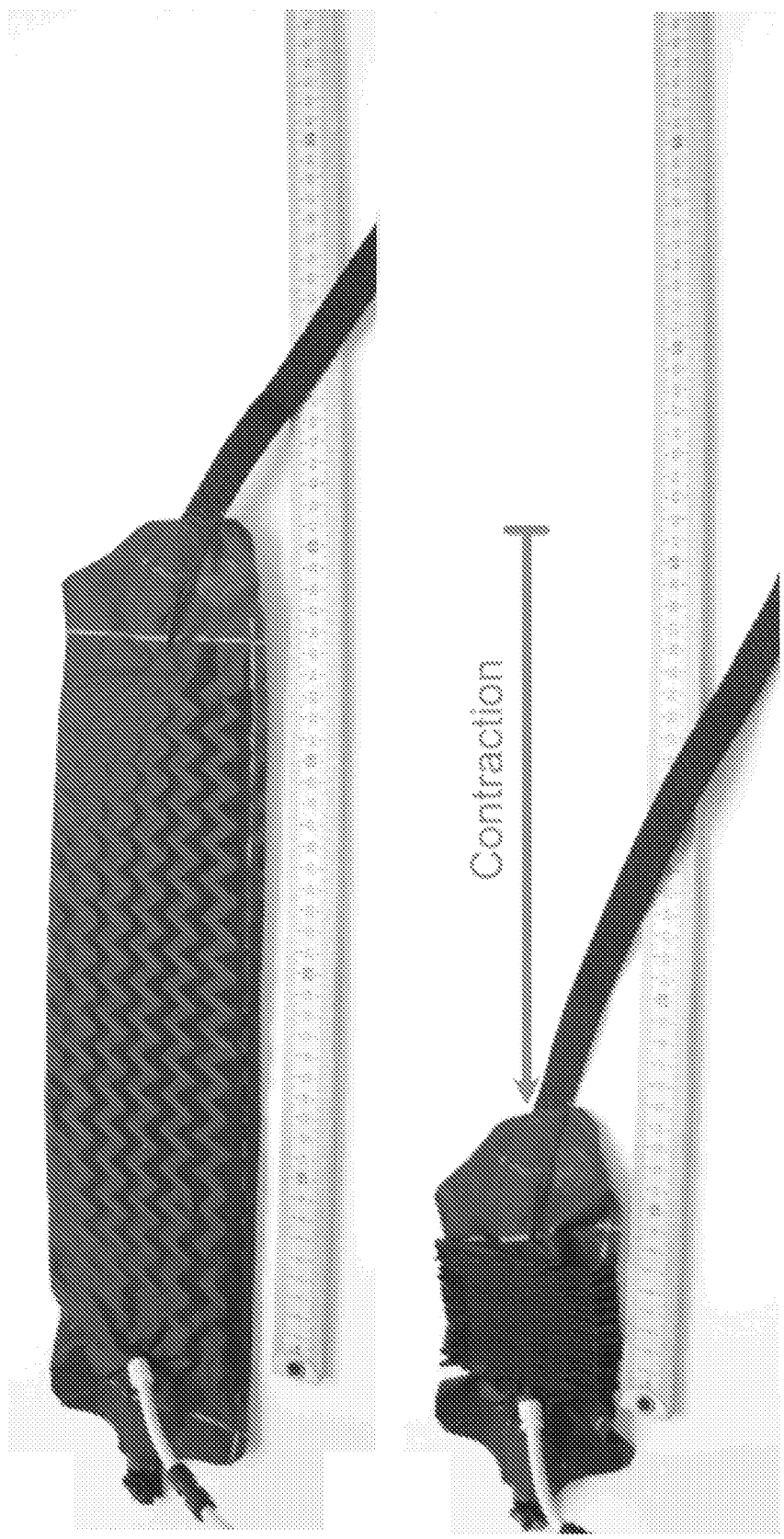
FIG. 8 is a photograph of one non-limiting example of a flexible actuator used in one non-limiting experimental design accordance with the present disclosure.

Referring to FIG. 8, a particular experimental design of the soft patient control unit was created using a thin plastic film perforated, folded in the Miura fold pattern, and then sealed in an airtight skin with an air hose connector and a connection strap at both ends. The upper image shows the unit in ambient air, whereas the lower image shows the unit contracted, which is predefined by the fold pattern of the plastic film.

Figure 9:
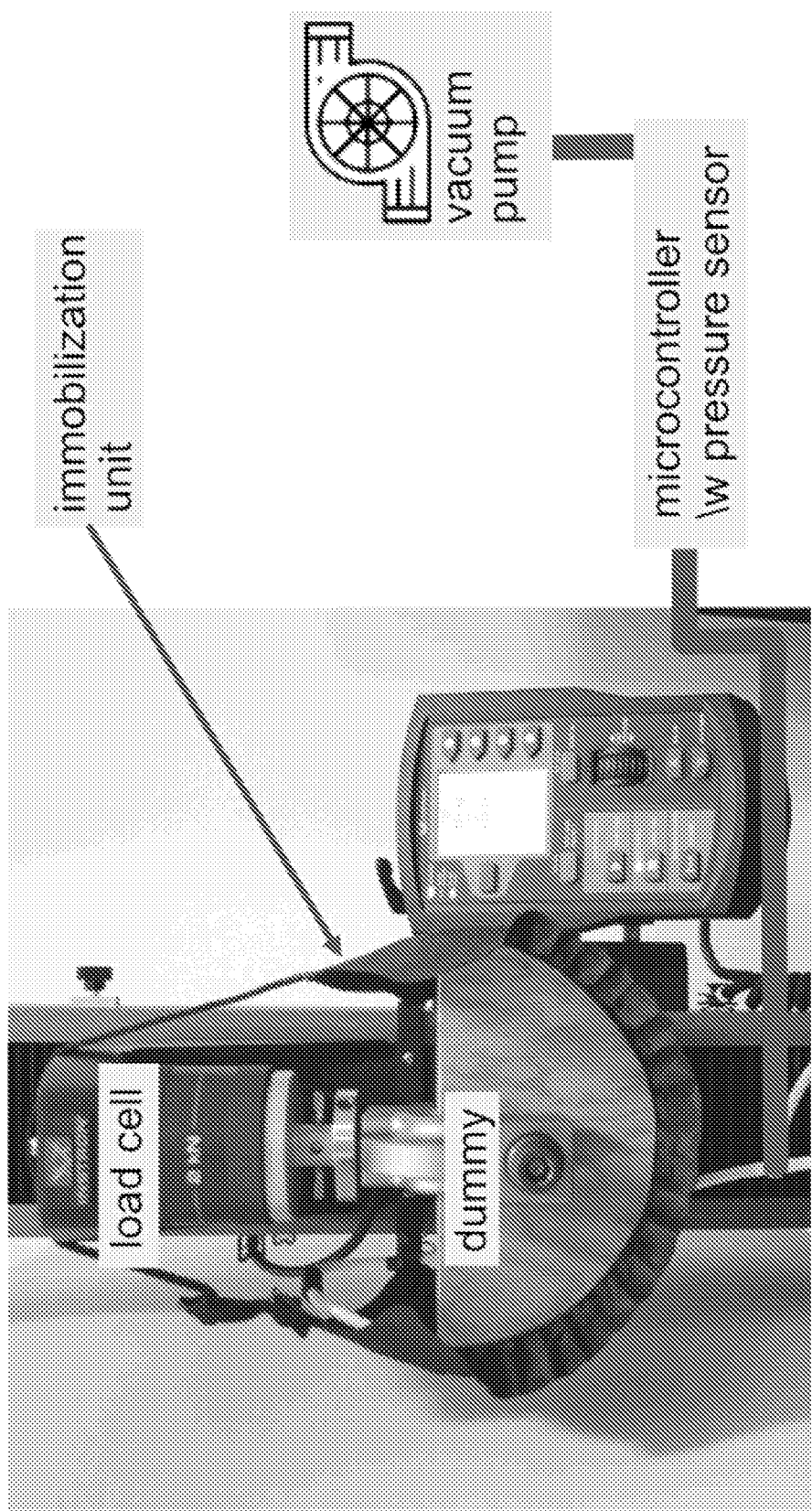
FIG. 9 is a modified photograph of an experimental setup of a flexible actuator designed to serve as shoulder immobilization and repositioning unit attached to the 2kN load cell for testing in accordance with one non-limiting experimental design in accordance with the present disclosure.

Referring to FIG. 9, a load cell was constructed to test the flexible actuator as a patient control system using an Instron 5944 (Instron, U.S.A.). A custom-made wooden half cylinder was used to mimic a body part which is held down by the unit. For pressure monitoring, an Arduino UNO with a pressure sensor was used.

To characterize a single, soft patient control unit, the contraction ratio of the unit was first determined by evacuating the unit to (−99±1) kPa. A contraction ratio of approximately 75% was achieved. In a subsequent experiment, the holding force in relation to the applied pressure was investigated. A phantom representing the human shoulder region was made of sheet wood (half circle with radius of (20.0±0.1) cm) and attached to the load cell of an Instron 5944 (Instron, U.S.A) universal testing machine. The patient control unit was connected to a vacuum pump with a regulator and air pressure sensor attached. The pressure was regulated to vary the pressure difference between the device pressure and atmospheric pressure, while the load cell was monitored.

Figure 10:
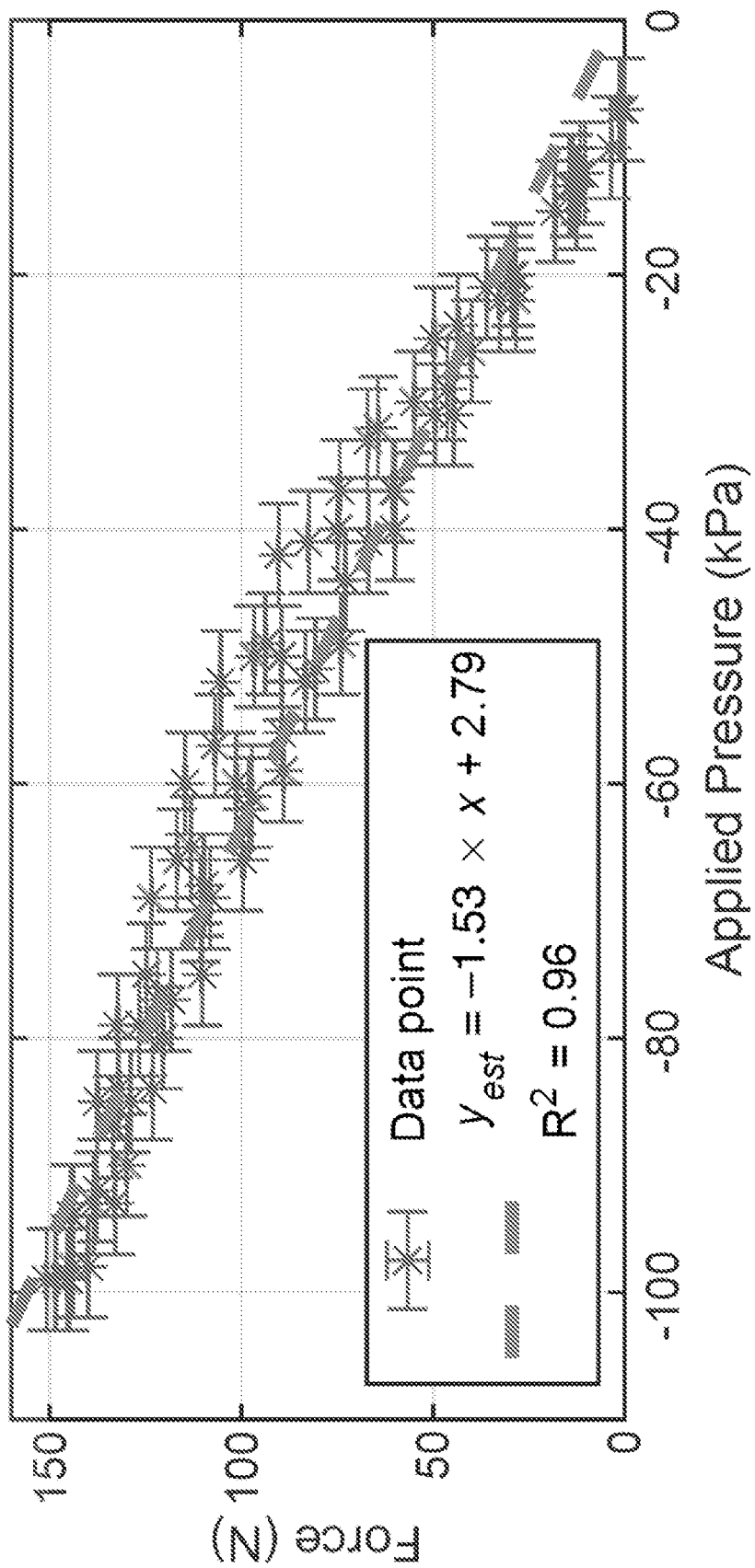
FIG. 10 is a graph of the attainable holding force for different levels of vacuum pressure of one non-limiting experimental design in accordance with the present disclosure.
Figure 11A:
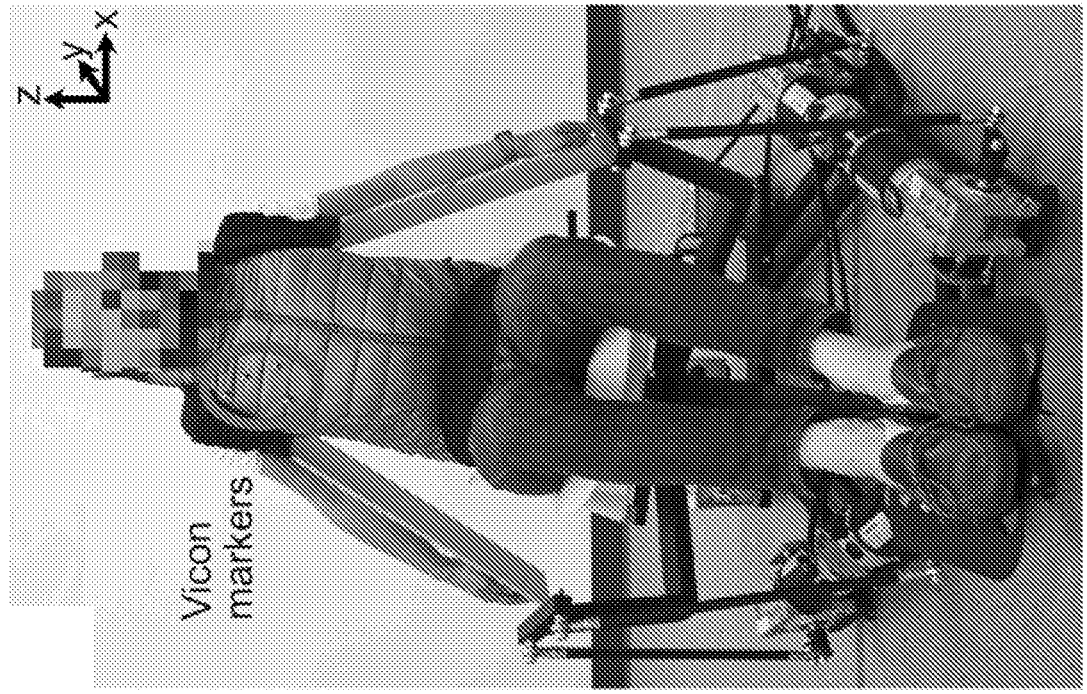
FIG. 11A is a photograph of a volunteer for one non-limiting experimental design sitting on the upright patient chair with one non-limiting example of a flexible actuator controlled and monitored by a system in accordance with the present disclosure relative to a region of interest (ROI) for position monitoring on the right chest.
Figure 11B:
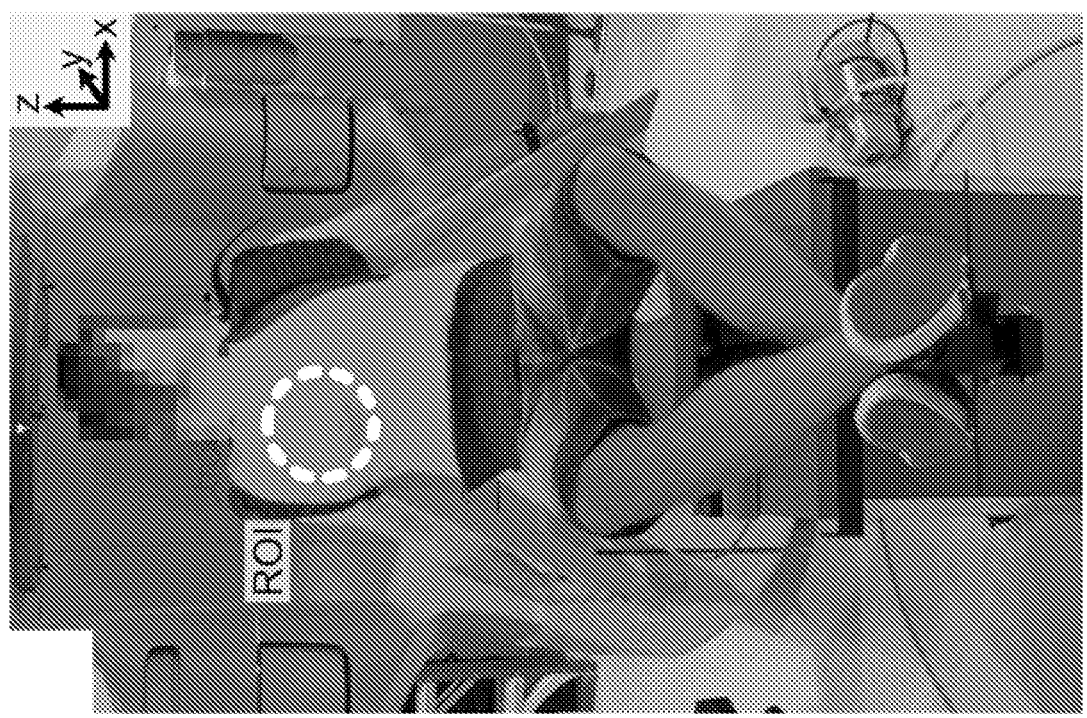
FIG. 11B is a photograph of a volunteer for one non-limiting experimental design seated in a patient positioning system in accordance with the present disclosure and in a tilted position of 8.6° in the roll direction with the flexible actuator engaged with the shoulder region, which is monitored by markers that were attached to the chest region.
Figures 12A, 12B, 12C:
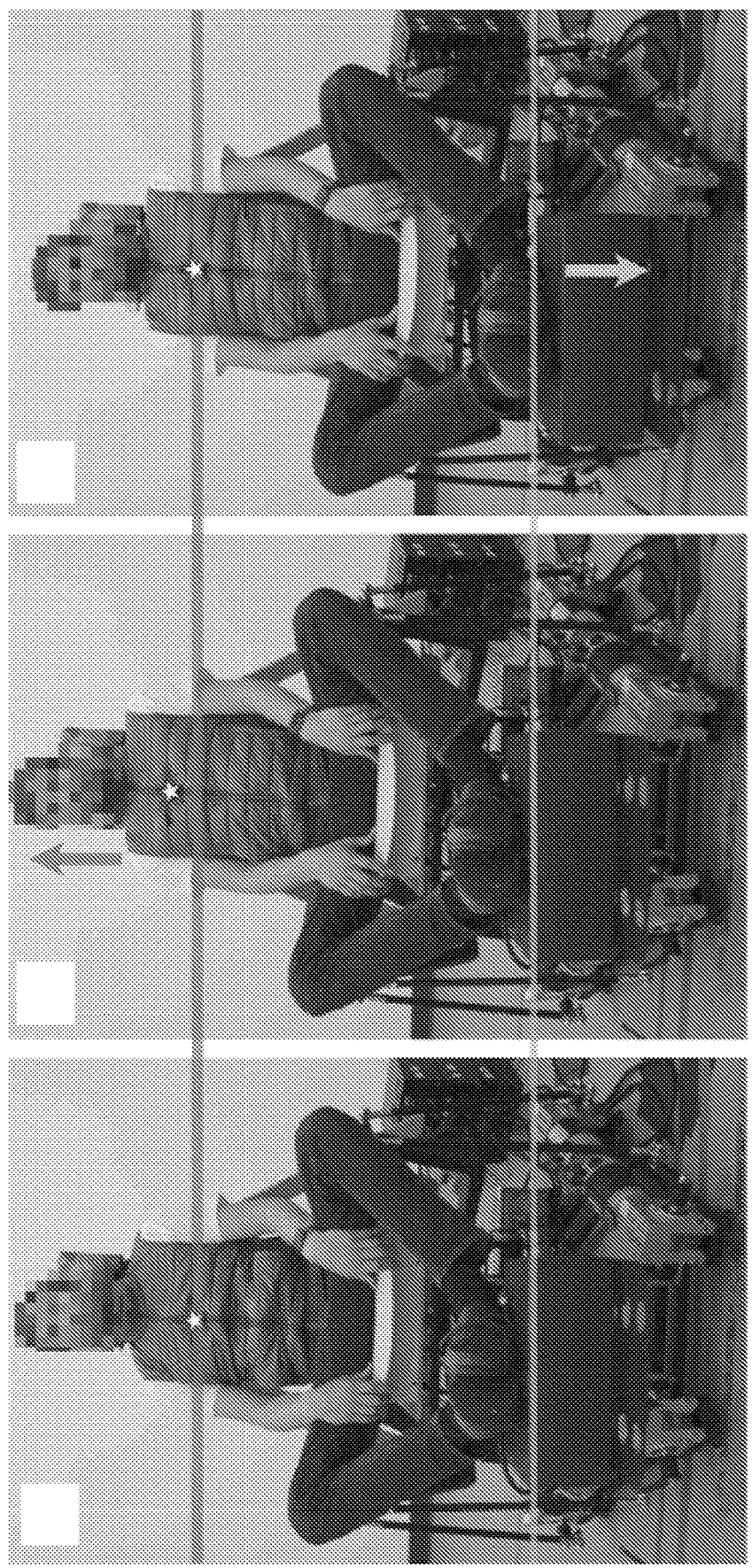
FIG. 12A is a photograph of a volunteer for one non-limiting experimental design sitting on the patient positioning system with a marker (starred) attached.
FIG. 12B is a photograph of the volunteer of FIG. 12A moving the body upwards.
FIG. 12C is a photograph of the volunteer of FIG. 12B showing that the system in accordance with the present disclosure corrects for the movement of the volunteer.

For each of the 80 different pressure differences tested, the force registered by the load cell as shown in the pressure-force plot in FIG. 10. A maximum force of (150±4) N was achieved at (99±1) kPa. A linear relation between pressure and force was observed with a small hysteresis effect.

Referring to FIGS. 11A, 11B, 12A, 12B, and 12C, the robotic patient positioner developed in this study used a Gough-Stewart platform and a patient chair. A commercial Stewart platform (DOF Reality, Corp.) designed for driving and flying simulations was adapted as the base of the patient positioner. The six rotary actuators of the system work in pairs connected to a motor driver each controlled by a microcontroller (Arduino UNO, Italy).

For this study the patient chair mounted on top of the Stewart platform was designed specifically for breast cancer treatment. The chair has height adjustable arm supports for lateral arm placement that provides support under the arm and in the armpit region to prevent slouching. A plastic headrest was attached to the top of the chair's backrest. T-slotted aluminum rails, in the respective hip and shoulder region of the chair, function as height and width adjustable points of connection for the patient control units.

We developed a plugin to the platform's software. It allows a MATLAB (MathWorks Inc., U.S.A.) script to control the platform. The data stream from the Vicon tracker system (Vicon Motion Systems, U.K.) was analyzed within the same script. This data stream was used as feedback for a proportional controller that was implemented to accurately control the position of the platform. A calibration routine was written to automatically calibrate the system and transform position vectors from the Vicon coordinate system to the robot coordinate system.

This set of experiments evaluated the effectiveness of the soft patient control device by measuring the movement of a selected regions-of-interest (ROI) on the body of immobilized healthy volunteers. The first part of the experiment was conducted in a radiation treatment room at Massachusetts General Hospital (MGH) (Boston, U.S.A.) with the patient control device attached to the patient chair placed on top of a cabinet. The treatment room is equipped with AlignRT (VisionRT, U.K.), an FDA approved optical motion tracking system for radiation therapy that evaluates changes in position of a ROI in 6 DOF to sub-millimeter accuracy. The system provides a 3D surface image of a volunteer using triangulation. The AlignRT system comprises an operation computer and three camera stations on the ceiling. Each of the camera stations contains two stereoscopic cameras, a speckle projector, and a texture camera.

In order to compare the effectiveness of the system, a group of volunteers sitting on the patient chair was positioned at the isocenter which is the place that the AlignRT has its highest accuracy. The group consisted of one female and four male volunteers with a body height between 160 cm and 195 cm, weight between 50 kg and 90 kg, Two measurements, each of 15 min, were performed for every volunteer. One measurement with the patient control device and one without it. A breast phantom made of foam and covered in white tape for better detectability by the AlignRT was attached to the chest region of the volunteer with tape. Volunteers were instructed to wear tight clothes to ensure minimum movement between clothes and body. A reference image of the volunteers' body surface was taken and a ROI was selected similar to the clinical procedure. For the duration of the measurement, AlignRT recorded the position changes of the ROI in 6 DOF at a frame rate between 5 Hz and 6 Hz.

The second part of the experiment was conducted in a room equipped with a Vicon tracker system due to limited space at the hospital treatment room for the 6 DOF robot. The robotic patient positioner was used to tilt the chair with the volunteer to its maximum angle of 8.6° in the roll direction. The experiment was then conducted without and with the patient control device on for a measurement of 15 min. The Vicon tracker system uses 10 infrared cameras with infrared spotlights to illuminate their field of view. The system was calibrated to track positions to sub-millimeter accuracy in 3 dimensions for a single reflective marker and up to 6 dimensions for multiple reflective markers grouped as an object. The chest wall region of the volunteer was contoured with four reflective markers which were grouped together to measure changes in all 6 DOF.

In this experiment the robotic patient positioner's ability to correct for changes in the position was evaluated. First the robot was tested without a human payload to evaluate the limitations of the controller rather than the hardware, when under load. A change in position was simulated by attaching a Vicon marker to the chair and activating the controller set to hold the marker in position. The position of the marker was monitored by the Vicon tracker system while the controller moved the patient chair to reposition the marker.

In the next test, a volunteer was seated on the patient chair and a Vicon marker was attached to the chest region. The volunteer moved the body upwards and the motion of the marker was recorded.

Figure 13:
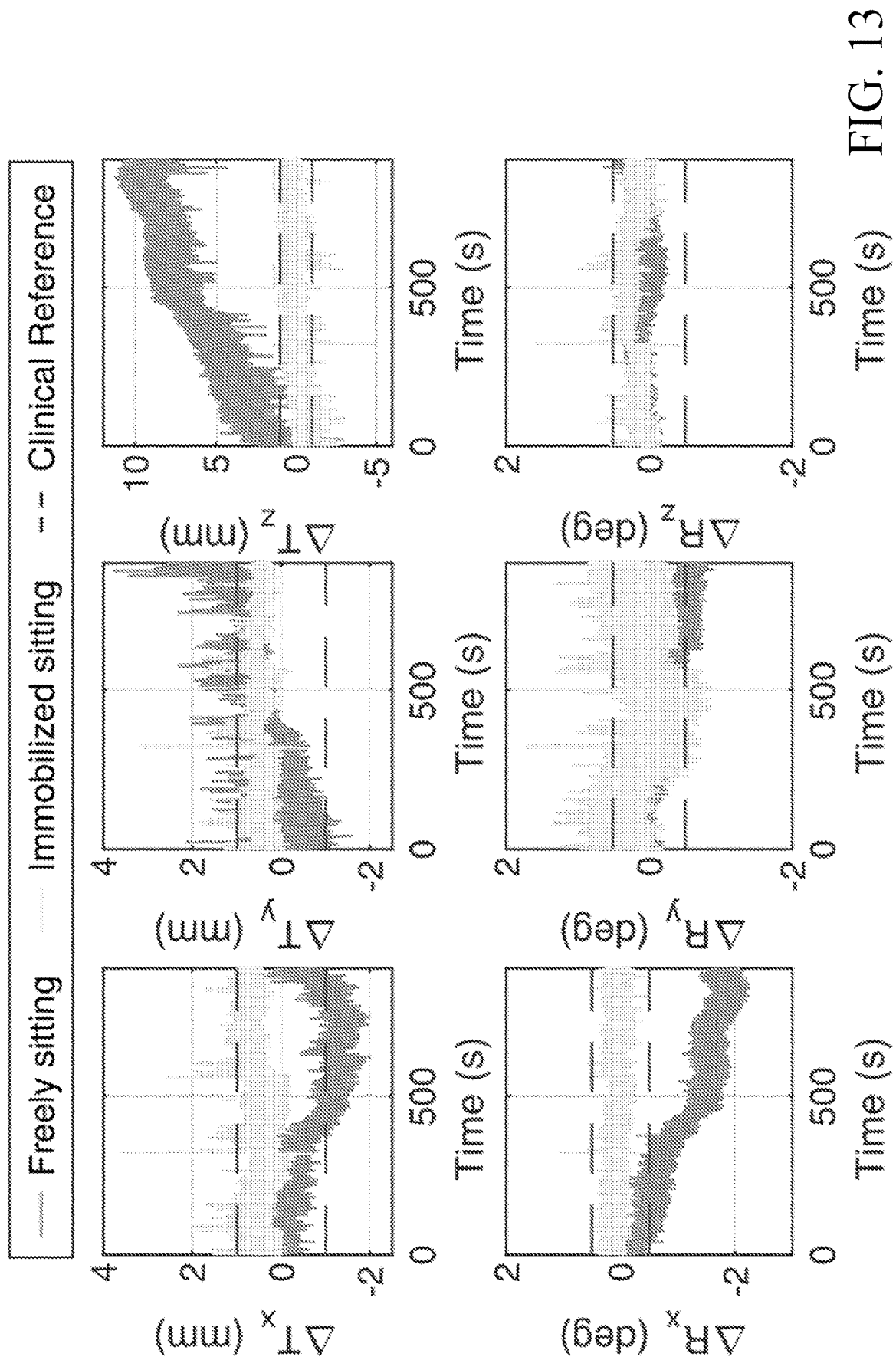
FIG. 13 is a series of graphs evaluating the flexible actuator on one volunteer in one non-limiting experimental study. The curves correspond to the measurement without and with the soft robotic immobilization and positioning device. The black horizontal lines on each figure are the clinical positioning accuracy requirement of 1 mm and 0.5°. The respiratory pattern can be seen as the high frequency variations.

FIG. 13 shows the results of the immobilization and repositioning evaluation for one of the five volunteers sitting in an upright chair position. The blue line and the pink line indicate the position change without and with the patient control device, respectively. The first row shows the changes in position in x, y, and z-direction. The x, y, and z-direction are along the body lateral direction, anterior-posterior, and superior-inferior, respectively. The second row shows the rotational changes in pitch (Rx), roll (Ry) and yaw (Rz) direction. The dashed horizontal black lines in each plot indicate the clinical required position accuracy of 1 mm and 0.5°. The high frequency variations displayed especially in the z-direction are the chest wall motions due to the breathing of the volunteers. This breathing pattern is less prominent with the soft patient control device for some volunteers.

Figure 14:
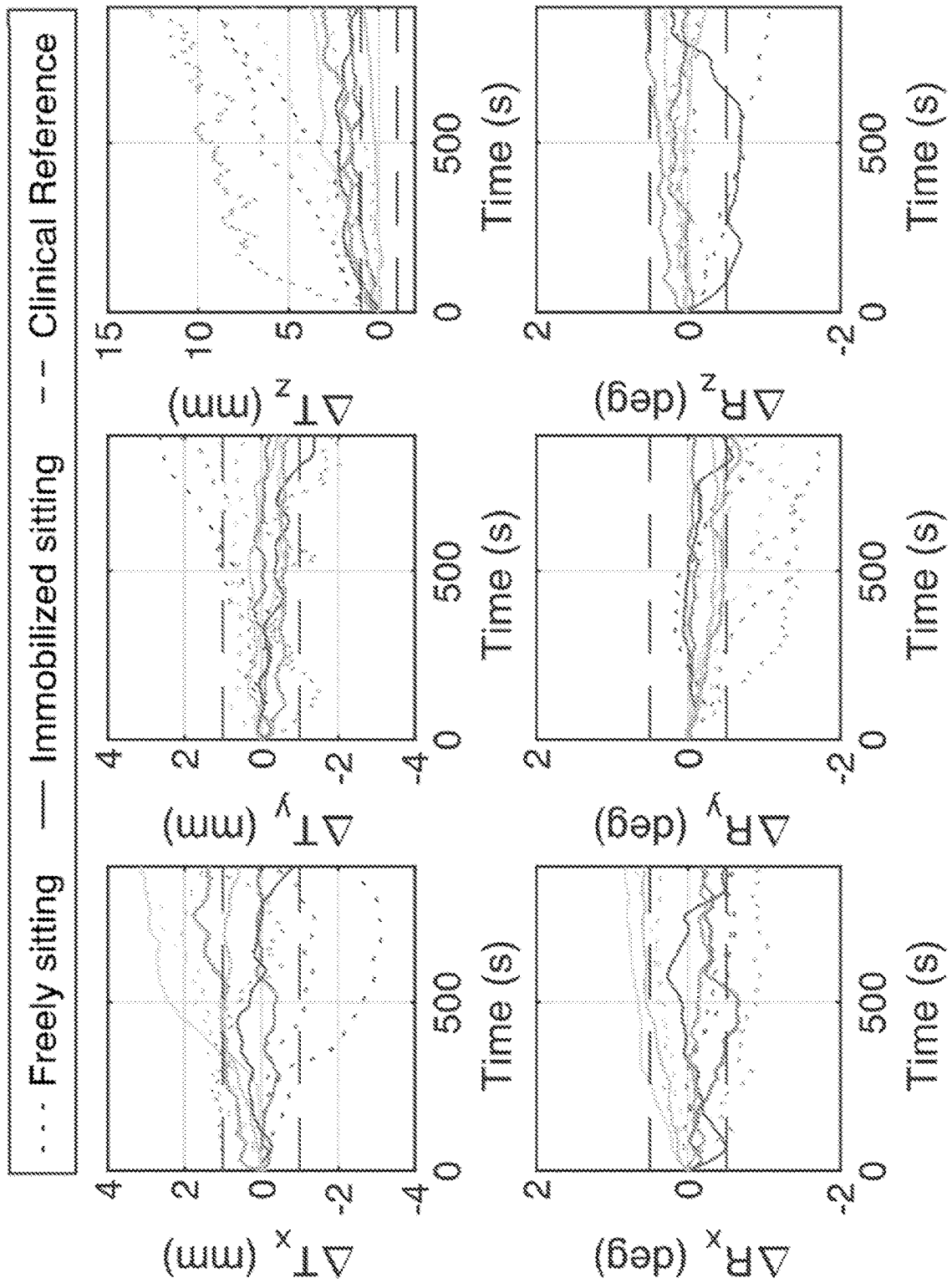
FIG. 14 is a series of graphs from one non-limiting experimental study to evaluate the flexible actuator for a group of volunteers. This data was filtered with a Savitsky-Golay filter. Same color lines represent the same volunteer without (dotted line) and with (solid line) the soft immobilization and positioning device.

We used Savitzky-Golay filtering on the monitoring data to obtain the long-term trends in the patient position. The position trend for five volunteers are shown in FIG. 14 for a better comparison. For all five volunteers, our soft patient control device shows a promising reduction in the position change over 15 minutes. The motion in the z-direction is more prominent than other directions. The z-direction is the direction which the slouching happens. Only two volunteers' position changes are within 1 mm in the z-direction during the 15 minutes monitoring. This result motivates us to develop the controller for the robotic positioner to further correct the position change to meet the clinical requirement. All volunteers with immobilization meet the 1 mm and 0.5° requirement in the y-direction and the three rotations directions. For the x-direction, two volunteers don't meet the 1 mm requirement.

The results of the immobilization and positioning evaluation in tilted position of 8.6° roll angle are shown in FIG. 14. The volunteers' motion without the patient control device in all translations and rotations are out of the tolerance. The motion with the immobilization in x direction and the rotation around y and z-axis are out of 1 mm and 0.5°tolerance by a small amount. We could correct this position change with the controller on the robotic patient positioner.

Figure 15:
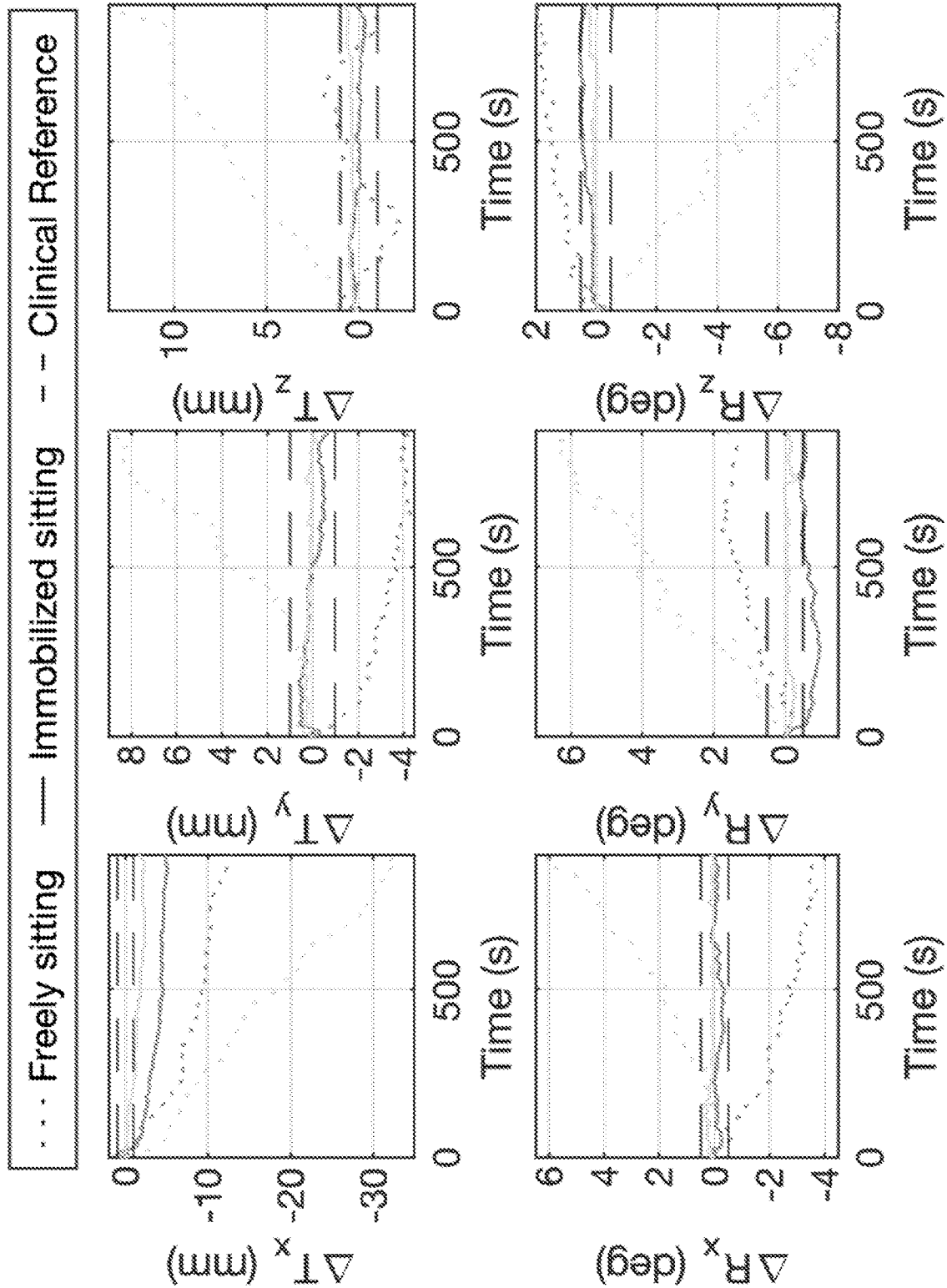
FIG. 15 is a series of graphs from one non-limiting experimental study evaluating the flexible actuator with two volunteers in 8.6° tilted position. The data was filtered with a Savitsky-Golay filter. Same color lines represented the same volunteer without (dotted line) and with (solide line) the soft immobilization and positioning device.
Figure 16:
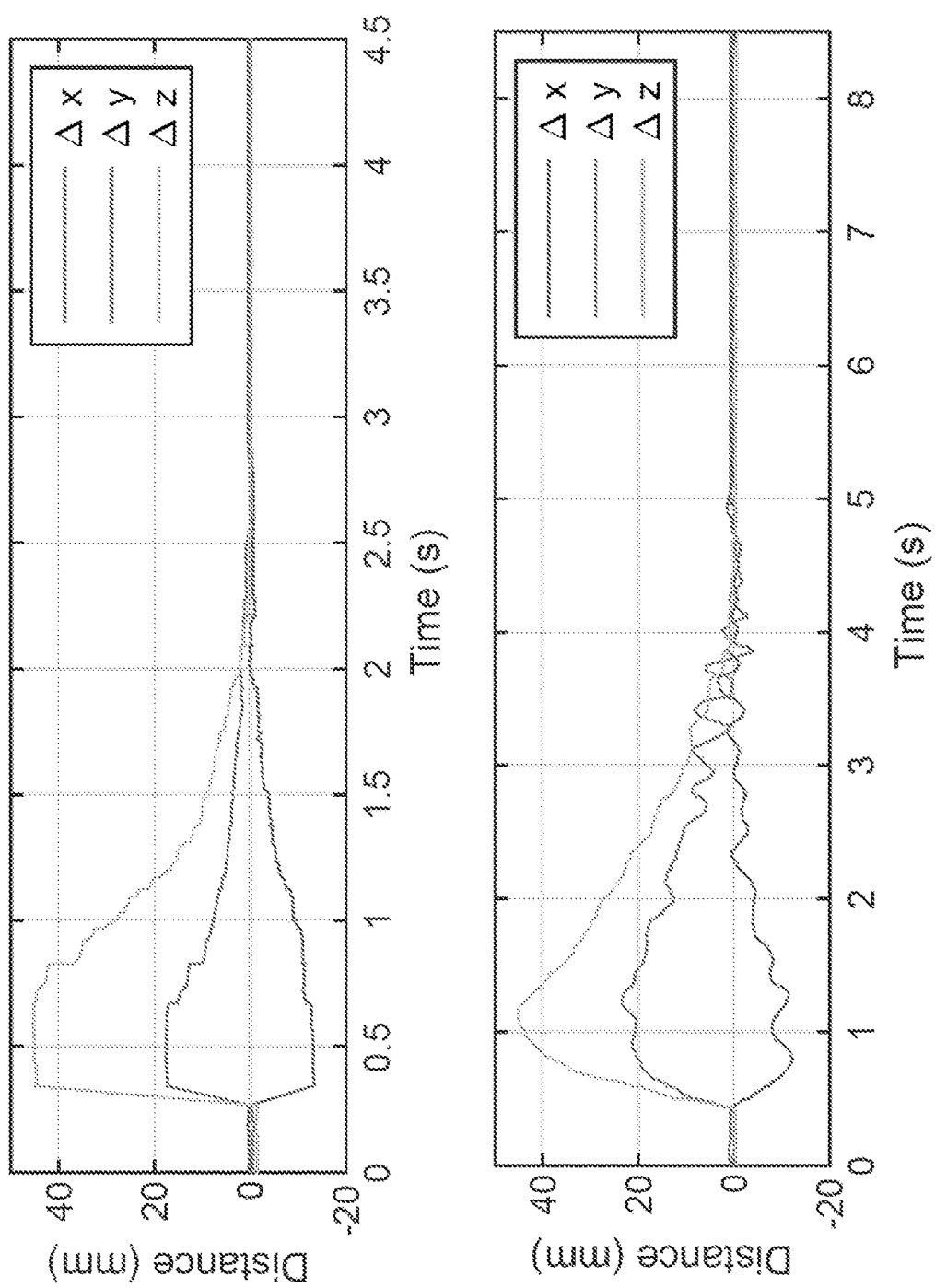
FIG. 16 is a pair of graphs from one non-limiting experimental study of the change in position for 3 degrees of freedom studied in a motion correction experiment (upper graph) and with a volunteer (lower graph). For the upper graph, after 0.25 seconds the marker was moved by 45 mm and the position was corrected to ±1 mm within 2 seconds. For the lower graph, after 0.5 seconds the marker was moved and within 4.5 seconds the position was corrected within 1 mm.

In the first part of the experiment without a volunteer on the patient chair, the marker was moved up by about 45 mm and the controller corrected to 1 mm within 2 s as shown in FIG. 15. This shows that the controller can correct and hold the position of a marker in 3D at a speed of (22.5 mm/s), which is much faster than the slouching movement with a speed of (0.05 mm/s) that was detected during the evaluation of the patient control device.

Even with a volunteer sitting on the patient chair, the results shows the robotic patient positioner's ability to correct a 45 mm change in position within 4.5 sections, within the ±1 mm desired tolerance. This indicates that the slow drift identified as slouching in section V-A with a maximum slouching motion of 0.05 mms$^{-1}$ can be corrected by the controller acting on average at 10 mms$^{-1}$. The experiment showed that a proportional controller is sufficient for this task.

In this study, we proposed a more compact and more affordable proton therapy system through the development of a new soft robot system for patient immobilization and repositioning, which can provide a patient universal, an active control, an adaptive system. We described the design and fabrication approach of the soft patient control device. The experiments in this study compared the performances between the soft robot patient control device and no immobilization on healthy volunteers. These experiments showed that this device reduced the volunteer's slouching motion substantially. More experiments will be conducted to compare our soft patient control device with currently clinic used thermal plastic mask and a simple seat-belt like straps. These experiments shall also be performed for different tumor sites to determine the best solution for each disease site. For example, dedicated soft patient control devices for the head-and-neck region and the thoracic region will be designed and fabricated. In addition, actual patients testing of the device will be performed to evaluate if the current soft robot patient control device is suitable for patients who might be weaker than healthy volunteers. Based on the future patients testing, different folding patterns and materials that allow for more patient comfort may be warranted.

In this study, we also presented the development of the robotic base and patient chair prototype which provided accurate positioning and the integration of the system. The 6 DOF parallel robot system and controller in this study are a basic system providing the functionality for initial evaluation of the newly developed soft robot patient control device. A more advanced robotic and control system will be developed in the future to integrate with the patient control device for the next stage prototype. For example, an actuated slewing ring to allow for 360° yaw rotation as well as an adaptable backrest tilt mechanism are needed. This study also provides opportunities for future work on a more sophisticated controller to correct for respiratory motion.

Even though more experiments and iterations of the prototype are necessary to develop the final product, this study has shown that soft robot can be utilized for patient immobilization in sitting and reclined positions to achieve required clinical positioning tolerance of 1 mm and 0.5° for compact gantry-less proton therapy system.

The present disclosure has described one or more preferred non-limiting examples, and it should be appreciated that many equivalents, alternatives, variations, and modifications, aside from those expressly stated, are possible and within the scope of the invention.

It is to be understood that the disclosure is not limited in its application to the details of construction and the arrangement of components set forth in the following description or illustrated in the following drawings. The disclosure is capable of other non-limiting examples and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

As used herein, unless otherwise limited or defined, discussion of particular directions is provided by example only, with regard to particular non-limiting examples or relevant illustrations. For example, discussion of "top," "front," or "back" features is generally intended as a description only of the orientation of such features relative to a reference frame of a particular example or illustration. Correspondingly, for example, a "top" feature may sometimes be disposed below a "bottom" feature (and so on), in some arrangements or non-limiting examples. Further, references to particular rotational or other movements (e.g., counterclockwise rotation) is generally intended as a description only of movement relative a reference frame of a particular example of illustration.

In some non-limiting examples, aspects of the disclosure, including computerized implementations of methods according to the disclosure, can be implemented as a system, method, apparatus, or article of manufacture using standard programming or engineering techniques to produce software, firmware, hardware, or any combination thereof to control a processor device (e.g., a serial or parallel general purpose or specialized processor chip, a single- or multi-core chip, a microprocessor, a field programmable gate array, any variety of combinations of a control unit, arithmetic logic unit, and processor register, and so on), a computer (e.g., a processor device operatively coupled to a memory), or another electronically operated controller to implement aspects detailed herein. Accordingly, for example, non-limiting examples of the disclosure can be implemented as a set of instructions, tangibly embodied on a non-transitory computer-readable media, such that a processor device can implement the instructions based upon reading the instructions from the computer-readable media. Some non-limiting examples of the disclosure can include (or utilize) a control device such as an automation device, a special purpose or general purpose computer including various computer hardware, software, firmware, and so on, consistent with the discussion below. As specific examples, a control device can include a processor, a microcontroller, a field-programmable gate array, a programmable logic controller, logic gates etc., and other typical components that are known in the art for implementation of appropriate functionality (e.g., memory, communication systems, power sources, user interfaces and other inputs, etc.).

The term "article of manufacture" as used herein is intended to encompass a computer program accessible from any computer-readable device, carrier (e.g., non-transitory signals), or media (e.g., non-transitory media). For example, computer-readable media can include but are not limited to magnetic storage devices (e.g., hard disk, floppy disk, magnetic strips, and so on), optical disks (e.g., compact disk (CD), digital versatile disk (DVD), and so on), smart cards, and flash memory devices (e.g., card, stick, and so on). Additionally it should be appreciated that a carrier wave can be employed to carry computer-readable electronic data such as those used in transmitting and receiving electronic mail or in accessing a network such as the Internet or a local area network (LAN). Those skilled in the art will recognize that many modifications may be made to these configurations without departing from the scope or spirit of the claimed subject matter.

Certain operations of methods according to the disclosure, or of systems executing those methods, may be represented schematically in the FIGS. or otherwise discussed herein. Unless otherwise specified or limited, representation in the FIGS. of particular operations in particular spatial order may not necessarily require those operations to be executed in a particular sequence corresponding to the particular spatial order. Correspondingly, certain operations represented in the FIGS., or otherwise disclosed herein, can be executed in different orders than are expressly illustrated or described, as appropriate for particular non-limiting examples of the disclosure. Further, in some non-limiting examples, certain operations can be executed in parallel, including by dedicated parallel processing devices, or separate computing devices configured to interoperate as part of a large system.

As used herein in the context of computer implementation, unless otherwise specified or limited, the terms "component," "system," "module," and the like are intended to encompass part or all of computer-related systems that include hardware, software, a combination of hardware and software, or software in execution. For example, a component may be, but is not limited to being, a processor device, a process being executed (or executable) by a processor device, an object, an executable, a thread of execution, a computer program, or a computer. By way of illustration, both an application running on a computer and the computer can be a component. One or more components (or system, module, and so on) may reside within a process or thread of execution, may be localized on one computer, may be distributed between two or more computers or other processor devices, or may be included within another component (or system, module, and so on).

In some implementations, devices or systems disclosed herein can be utilized or installed using methods embodying aspects of the disclosure. Correspondingly, description herein of particular features, capabilities, or intended purposes of a device or system is generally intended to inherently include disclosure of a method of using such features for the intended purposes, a method of implementing such capabilities, and a method of installing disclosed (or otherwise known) components to support these purposes or capabilities. Similarly, unless otherwise indicated or limited, discussion herein of any method of manufacturing or using a particular device or system, including installing the device or system, is intended to inherently include disclosure, as non-limiting examples of the disclosure, of the utilized features and implemented capabilities of such device or system.

As used herein, unless otherwise defined or limited, ordinal numbers are used herein for convenience of reference based generally on the order in which particular components are presented for the relevant part of the disclosure. In this regard, for example, designations such as "first," "second," etc., generally indicate only the order in which the relevant component is introduced for discussion and generally do not indicate or require a particular spatial arrangement, functional or structural primacy or order.

As used herein, unless otherwise defined or limited, directional terms are used for convenience of reference for discussion of particular figures or examples. For example, references to downward (or other) directions or top (or other) positions may be used to discuss aspects of a particular example or figure, but do not necessarily require similar orientation or geometry in all installations or configurations.

This discussion is presented to enable a person skilled in the art to make and use non-limiting examples of the disclosure. Various modifications to the illustrated examples will be readily apparent to those skilled in the art, and the generic principles herein can be applied to other examples and applications without departing from the principles disclosed herein. Thus, non-limiting examples of the disclosure are not intended to be limited to non-limiting examples shown, but are to be accorded the widest scope consistent with the principles and features disclosed herein and the claims below. The following detailed description is to be read with reference to the figures, in which like elements in different figures have like reference numerals. The figures, which are not necessarily to scale, depict selected examples and are not intended to limit the scope of the disclosure. Skilled artisans will recognize the examples provided herein have many useful alternatives and fall within the scope of the disclosure.

Various features and advantages of the disclosure are set forth in the following claims.

What is claimed is:

1. A system for delivering radiotherapy to a patient, the system comprising:
    a patient support structure configured to receive a patient during a radiotherapy process using a radiotherapy source to deliver a therapy to the patient when positioned on the patient support structure;
    a patient positioning system configured to adjust a position of the patient support structure relative to the radiotherapy source;
    a flexible actuator configured to secure the patient to the patient support and adjust a position of at least a portion of the patient relative to the patient support;
    an imaging system configured to acquire imaging data of the patient, the patient support, and the flexible actuator during the radiotherapy process;
    a computer system configured to:
       control adjustment of the flexible actuator in at least one dimension;
       receive the imaging data and direct the patient positioning system to adjust the position of the patient support structure during the radiotherapy process and direct the flexible actuator to immobilize the patient as the patient positioning system adjusts the position of the patient support structure and reposition at least the portion of the patient relative to a radiotherapy plan; and
    wherein the flexible actuator forms an artificial muscle that contracts in one direction.

2. The system of claim 1, wherein the radiotherapy plan incorporates a positioning of the patient relative to the radiotherapy source or adjustment of the particle beam to utilize a Bragg peak in the radiotherapy process.

3. The system of claim 1, wherein the computer system is configured to control adjustment of the flexible actuator in at least two dimensions, and further comprising a vacuum pump in fluid communication with the flexible actuator and in electrical communication with the controller to effectuate adjustment of the flexible actuator in the at least two dimensions.

4. The system of claim 1, wherein the computer system is further configured to direct the controller to adjusts the flexible actuator to counteract gravitational forces on the patient as the patient positioning system adjusts the position of the patient support structure relative to the radiotherapy source.

5. The system of claim 4, wherein the computer system is further configured to direct the controller to adjust the flexible actuator to reposition the patient to correct for gravitational forces on the patient when the patient positioning system adjusts the position of the patient support structure relative to the radiotherapy source.

6. The system of claim 1, wherein the radiotherapy source is configured to deliver radiotherapy using a fixed beam to a patient during a radiotherapy process and wherein the patient positioning system is configured to adjust a position of the patient support structure relative to the radiotherapy source in 3, 4, 5, or 6 degrees of freedom.

7. The system of claim 1, wherein the flexible actuator extends proximate to one or more of a waist of the patient and one or more shoulders of the patient.

8. The system of claim 1, wherein the flexible actuator that forms the artificial muscle contracts in the one direction and expands in another direction simultaneously.

9. The system of claim 1, wherein the flexible actuator includes a fluid-driven origami orifical muscle (FOAM) system.

10. The system of claim 9, wherein the FOAM system includes a Miura fold.

11. The system of claim 1, wherein the computer system is configured to control adjustment of the flexible actuator in at least two dimensions, and
    wherein the flexible actuator forms a strap extending over at least a portion of the patient and wherein the at least two dimensions includes an in-plane contraction across the strap and a direction transverse to the in-plane direction of the strap.

12. A system for delivering radiotherapy to a patient, the system comprising:
    a radiotherapy source configured to deliver radiotherapy using a fixed beam to a patient during a radiotherapy process;
    a patient support structure configured to receive the patient during the radiotherapy process;
    a patient positioning system configured to adjust a position of the patient support structure relative to the radiotherapy source;
    a flexible actuator configured to secure the patient to the patient support and adjust a position of at least a portion of the patient relative to the patient support;
    an imaging system configured to acquire imaging data of the patient, the patient support, and the flexible actuator during the radiotherapy process;
    a computer system configured to:
       control adjustment of the flexible actuator in at least one dimension;
       receive the imaging data and direct the patient positioning system to adjust the position of the patient support structure during the radiotherapy process and direct the flexible actuator to immobilize the patient as the patient positioning system adjusts the position of the patient support structure and reposition the at least the portion of the patient relative to a radiotherapy plan; and
wherein the flexible actuator forms an artificial muscle that contracts in one direction.

13. The system of claim 12, wherein the radiotherapy source is a particle radiotherapy system.

14. The system of claim 12, wherein the computer system is further configured to direct the controller to adjusts the flexible actuator to counteract gravitational forces on the patient as the patient positioning system adjusts the position of the patient support structure relative to the radiotherapy source.

15. The system of claim 12, wherein the computer system is further configured to direct the controller to adjust the flexible actuator to reposition the patient to correct for gravitational forces on the patient when the patient positioning system adjusts the position of the patient support structure relative to the radiotherapy source.

16. The system of claim 12, wherein the flexible actuator that forms the artificial muscle contracts in the one direction and expands in another direction simultaneously.

17. The system of claim 12, wherein the flexible actuator includes a fluid-driven origami orifical muscle (FOAM) system.

18. The system of claim 12, wherein the computer system is configured to control adjustment of the flexible actuator in at least two dimensions, and
wherein the flexible actuator forms a strap extending over at least a portion of the patient and wherein the at least two dimensions includes an in-plane contraction across the strap and a direction transverse to the in-plane direction of the strap.

19. The system of claim 12, wherein the portion of the patient includes a target region identified in the radiotherapy plan.

20. A method for restraining and repositioning a patient during a radiotherapy procedure, the method including steps comprising:
   i) determining a current position of a patient on a patient support, wherein the patient is positioned to receive radiotherapy from a radiotherapy source during a radiotherapy process following a radiotherapy plan that includes a relative position of the patient to the radiotherapy source;
   ii) repositioning the patient during the radiotherapy process using a patient positioning system configured to adjust a position of the patient support structure relative to the radiotherapy source;
   iii) controlling a flexible actuator forming an artificial muscle that contracts in one direction that secures the patient to the patient support and adjust a position of the patient relative to the patient support using a controller to control adjustment of the flexible actuator in at least one dimension;
   iv) acquiring imaging data of the patient, the patient support, and the flexible actuator during the radiotherapy process; and
   v) analyzing the imaging data relative to the radiotherapy plan to determine an updated position of the patient relative to the radiotherapy plan; and
   vi) repositioning the patient using the flexible actuator to match a further updated position of the patient with the radiotherapy plan.

21. The method of claim 20, wherein steps i) through vi) are performed by a computer system.

22. The method of claim 20, further comprising controlling the adjustment of the flexible actuator in at least two dimensions.

* * * * *